(12) United States Patent
Ho et al.

(10) Patent No.: US 12,097,389 B2
(45) Date of Patent: Sep. 24, 2024

(54) TECHNIQUES FOR SKIN ILLUMINATION OF RADIATION THERAPY TREATMENT REGION USING NON-COAXIAL DIGITAL PROJECTOR

(71) Applicant: UNIVERSITY OF FLORIDA RESEARCH FOUNDATION, INCORPORATED, Gainesville, FL (US)

(72) Inventors: Meng Wei Ho, Jacksonville, FL (US); Zuofeng Li, Jacksonville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 1097 days.

(21) Appl. No.: 16/964,631

(22) PCT Filed: Jan. 25, 2019

(86) PCT No.: PCT/US2019/015186
§ 371 (c)(1),
(2) Date: Jul. 24, 2020

(87) PCT Pub. No.: WO2019/147961
PCT Pub. Date: Aug. 1, 2019

(65) Prior Publication Data
US 2021/0052919 A1 Feb. 25, 2021

Related U.S. Application Data

(60) Provisional application No. 62/622,498, filed on Jan. 26, 2018.

(51) Int. Cl.
*A61N 5/10* (2006.01)
*G06T 3/08* (2024.01)
(Continued)

(52) U.S. Cl.
CPC ......... *A61N 5/1049* (2013.01); *A61N 5/1081* (2013.01); *G06T 3/08* (2024.01);
(Continued)

(58) Field of Classification Search
CPC .. A61N 5/1049; A61N 5/1069; A61N 5/1075; A61N 5/1081; A61N 2005/1056;
(Continued)

(56) References Cited

U.S. PATENT DOCUMENTS

| 4,132,900 A | 1/1979 | Smith et al. |
| 4,726,046 A | 2/1988 | Nunan |

(Continued)

FOREIGN PATENT DOCUMENTS

| EP | 2123327 | * | 5/2013 | ........... A61N 5/1049 |
| EP | 1640922 B1 | | 7/2013 | |
| WO | 2007030142 A2 | | 3/2007 | |

OTHER PUBLICATIONS

PCT/US19/15186; International Search Report Written Opinion, dated May 17, 2019; 10 pages.
(Continued)

*Primary Examiner* — Carrie R Dorna
(74) *Attorney, Agent, or Firm* — Timothy H. Van Dyke; WOLTER, VAN DYKE, DAVIS, PLLC

(57) ABSTRACT

Techniques include receiving a treatment plan for a subject, including a body outline, a position on a couch, and, for each gantry angle, a couch angle an isocenter and target volumes to which a radiation source is directed. A perspective transform matrix is based on projected coordinates of reference points from a digital image projector onto each different plane perpendicular to a beam from the radiation source at different distances. Two-dimensional spot positions for a gantry and couch angle are determined based on the treatment plan. A group of spot positions are determined based (Continued)

on a common distance from the radiation source to the body outline. Illuminated spots on a projection image are determined based on the group and the perspective transform matrix closest to the common distance. The projection image is projected from the image projector onto the subject on the couch.

17 Claims, 17 Drawing Sheets

(51) Int. Cl.
    *G16H 20/40*     (2018.01)
    *G16H 30/40*     (2018.01)

(52) U.S. Cl.
    CPC ............. *G16H 20/40* (2018.01); *G16H 30/40* (2018.01); *A61N 2005/1056* (2013.01); *A61N 5/1075* (2013.01); *A61N 2005/1087* (2013.01)

(58) Field of Classification Search
    CPC ........... A61N 2005/1087; G16H 20/40; G16H 30/40; G06T 3/005
    See application file for complete search history.

(56) References Cited

U.S. PATENT DOCUMENTS

| | | | |
|---|---|---|---|
| 7,835,492 | B1 | 11/2010 | Sahadevan |
| 9,108,050 | B2 | 8/2015 | Bula et al. |
| 2009/0292200 | A1 | 11/2009 | Kindlein et al. |
| 2015/0036806 | A1* | 2/2015 | Wong .................. A61N 5/1075 |
| | | | 378/207 |

OTHER PUBLICATIONS

Lovchinsky, I. et al., "Nuclear magnetic resonance detection and spectroscopy of single proteins using quantum logic", Science, Feb. 19, 2016, vol. 351, issue 6275, pp. 836-841.

* cited by examiner

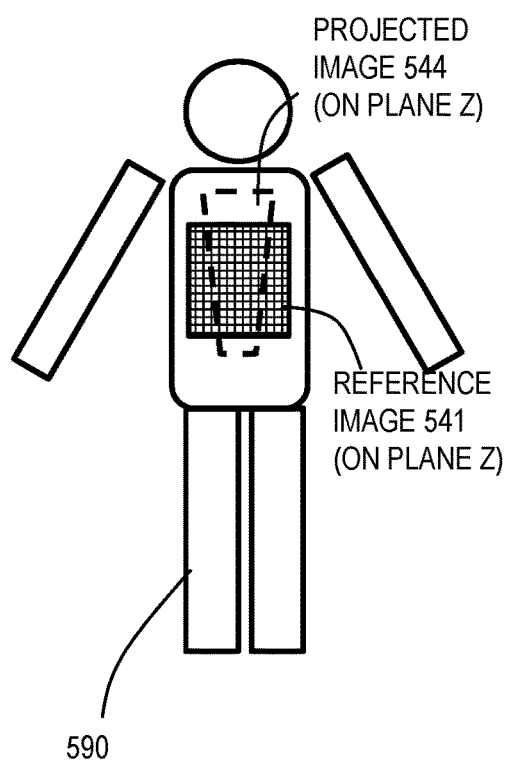
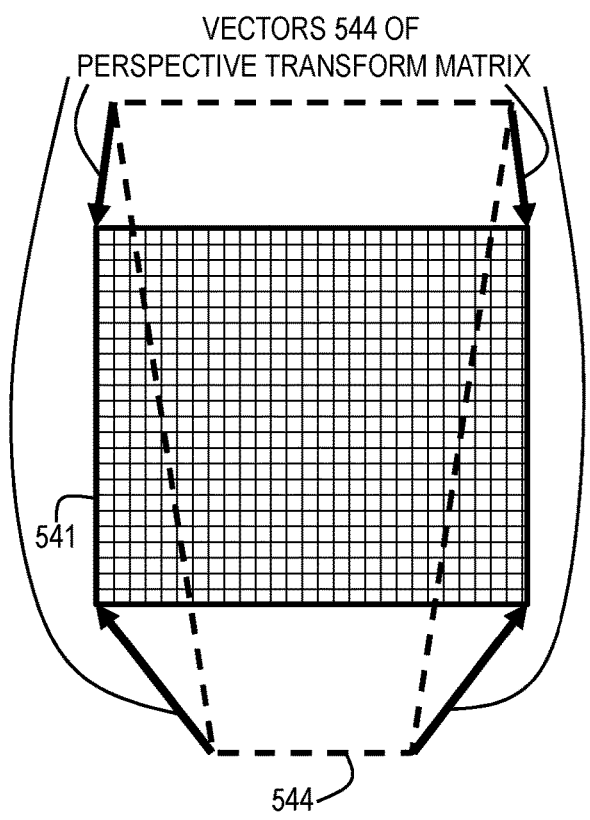
FIG. 5C
FIG. 5D

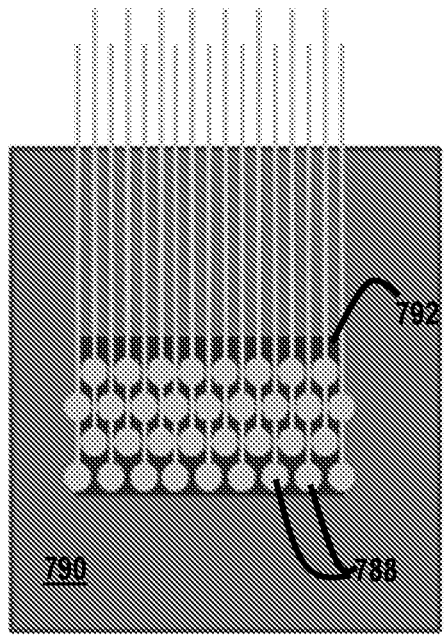
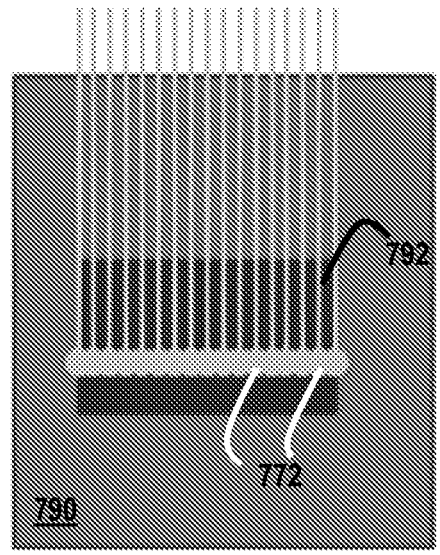
FIG. 7C  FIG. 7D
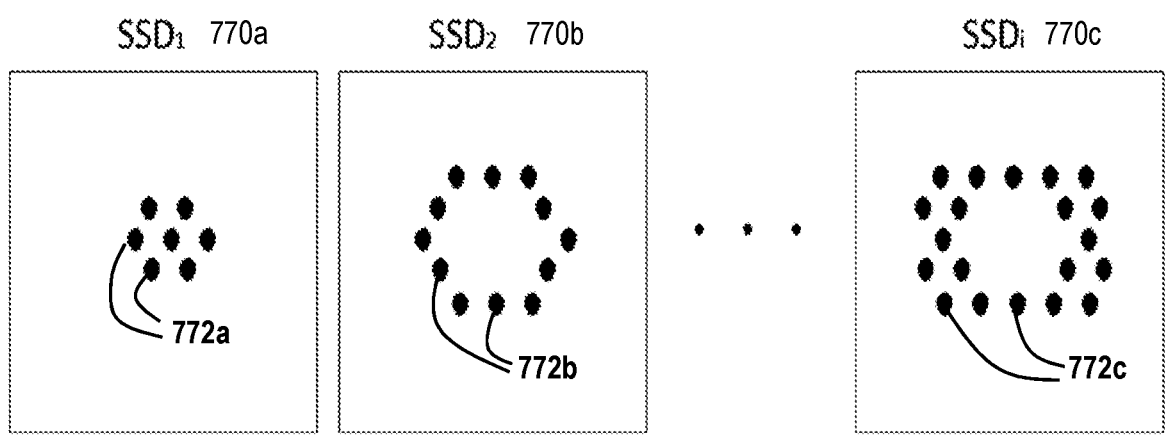
FIG. 7E

SURFACE POINT MAP IMAGE

PROJECTOR IMAGE pixel

774 cm/inch

776

TECHNIQUES FOR SKIN ILLUMINATION OF RADIATION THERAPY TREATMENT REGION USING NON-COAXIAL DIGITAL PROJECTOR

CROSS-REFERENCE TO RELATED APPLICATIONS

This application claims benefit of Provisional Appln. 62/622,498, filed Jan. 26, 2018, the entire contents of which are hereby incorporated by reference as if fully set forth herein, under 35 U.S.C. § 119(e).

BACKGROUND

Radiotherapy is a treatment for cancer patients involving the use of high-energy radiation, including particle beams such as proton beams. When high-energy radiation is delivered to a subject, it kills cells in the body. Although the high-energy radiation kills tumor cells in the subject's body, it may also kill normal tissue cells that surround the tumor. Thus, the goal of conventional radiotherapy is to deliver a sufficient radiation dose to the tumor to kill the tumor cells while minimizing the radiation dose delivered to the normal tissue cells that surround the tumor. This is accomplished, in general, by targeting the cancer cells repeatedly from different directions to accumulate a high dose at the tumor location while minimizing the dose to which other tissue is exposed. Before the radiation dose is delivered, it is advantageous to inform the operator of the area of the patient to be irradiated to allow the operator to verify both the treatment plan and the alignment of the patient in the radiotherapy apparatus.

SUMMARY

Techniques are provided for projecting a visible light image of areas to be irradiated, e.g., by a scanning particle pencil beam, onto patient skin during radiation therapy, such as for cancer treatment. The techniques allow review and verification to assure accuracy of patient treatment using such advanced radiotherapy technology. The areas to be irradiated on patient skin are calculated from treatment plans received from a radiotherapy treatment planning system. A miniature illuminating projection device, mounted on the radiotherapy treatment machine, projects the calculated irradiated treatment area onto the patient. The illuminated area is reviewed to assure that the treatment target is adequately covered daily, so as to eliminate treatment delivery errors.

In a first set of embodiments, a method includes receiving first data that indicates a perspective transform matrix corresponding to each of a plurality of different distances from a radiation source for particle therapy treatment. Each matrix is based on projected coordinates of a plurality of reference points from a digital image projector onto each of a plurality of different planes. The digital image projector is mounted on a rotating gantry to which is rigidly fixed an output port from the radiation source. Each of the plurality of different planes is perpendicular to an axis of a particle beam from the output port. The method also includes receiving second data that indicates a treatment plan for a subject, which includes a body outline of the subject, a position of the subject on a couch, and, for each of one or more gantry orientations, a couch angle, and a plurality of target volumes inside the subject to which particle beam therapy is directed. The method further includes determining automatically on a processor a plurality of two-dimensional (2D) spot positions for a gantry orientation and a couch angle based on the second data. The method even further includes determining automatically on the processor for the gantry orientation a group of the plurality of 2D spot positions based on a common distance from the radiation source to the body outline. The method still further includes determining automatically on the processor illuminated spots on a projection image based on the group of the plurality of 2D spot positions and the perspective transform matrix corresponding to a distance closest to the common distance. Even further, the method includes projecting the projection image from the image projector onto the subject on the couch when the gantry is at the gantry orientation and the couch is at the couch angle.

In some embodiments of the first set, steps are repeated for multiple different groups based on corresponding different common distances, before projecting the projection image. In some embodiments of the first set, steps are repeated for multiple different couch angles or gantry angles or both.

In some embodiments of the first set, determining spots on the projection image includes increasing the sizes of the at least some spots to at least partially fill spaces between the spots.

In other embodiments a computer-readable medium, apparatus or a system is configured to perform one or more steps of the above method.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 5C and FIG. 5D depict the difference between a computed reference image and the same image when projected on the skin of a subject, according to an embodiment;

FIG. 7C is a block diagram that illustrates example multiple target volumes from a treatment plan in a beam eye view (BEV), according to an embodiment;

FIG. 7D is a block diagram that illustrates example spots on the isocenter plane which correspond to the target volumes of FIG. 7C, according to an embodiment;

FIG. 7E is a set of plots that illustrate example spots on the spot map grouped by SSD values, according to an embodiment;

DETAILED DESCRIPTION

A method and apparatus are described for skin illumination of radiation therapy treatment region using a non-coaxial digital projector. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader rang around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments are described below in the context of scanning pencil beam particle therapy. However, the invention is not limited to this context. In other embodiments, the techniques are applied to other radiation sources, including x-ray or other photons, using pencil beams or diverging wide beams for therapy on live animals or plants or inanimate surrogates for same, or on other inanimate objects as subjects.

1. Overview of Hardware Components

Figure 1A:
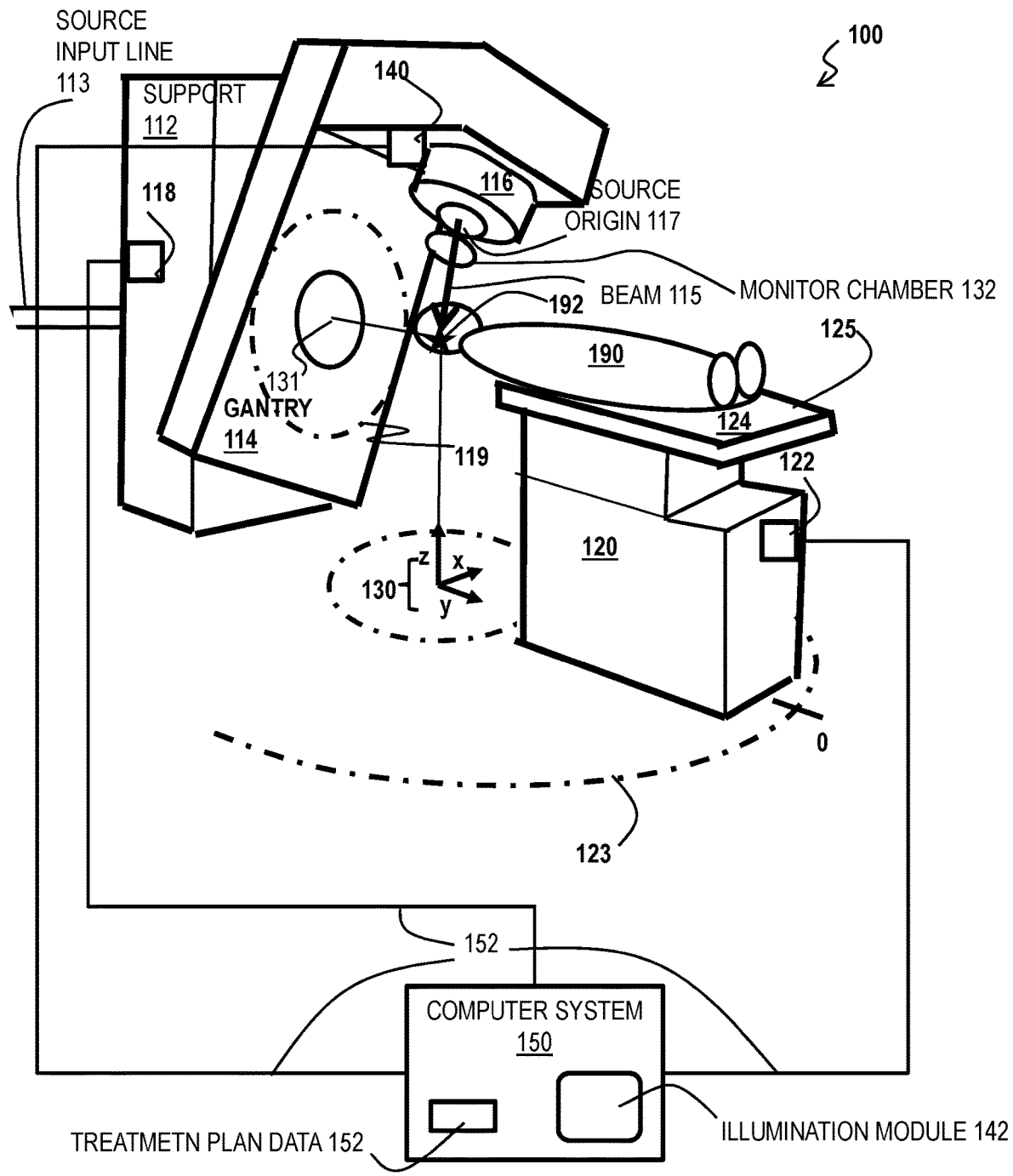
FIG. 1A and FIG. 1B are block diagrams that illustrate an example system for irradiation therapy, according to an embodiment.
Figure 1B:
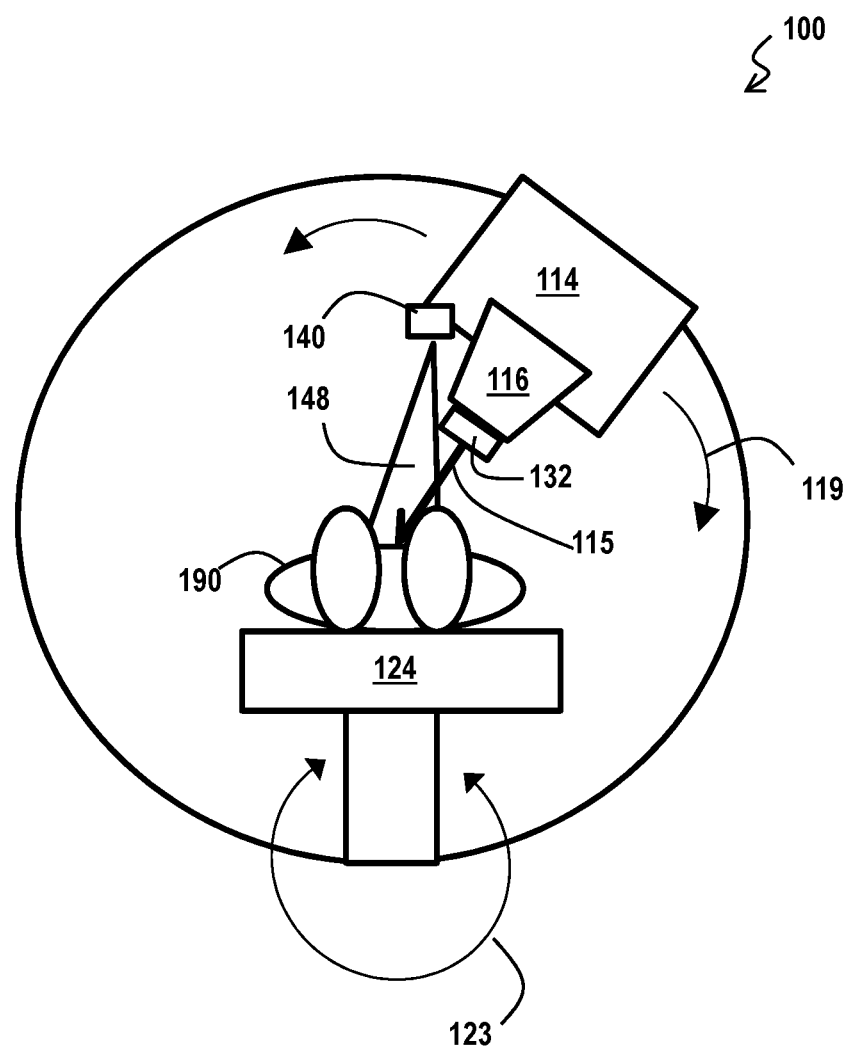

FIG. 1A and FIG. 1B are block diagrams that illustrate an example system 100 for irradiation, according to an embodiment. For purposes of illustration, a living subject 190 is depicted, but is not part of the system 100. As illustrated in FIG. 1A, a target region 192 is positioned within the subject 190. In an example embodiment, the target region 192 includes tumor cells. The system 100 includes a radiation source output port 116 at position 117, called a source origin, which emits a beam 115 that penetrates to the target area 192. In some embodiments, the radiation is generated in a separate accelerator and fed into the gantry 114 along source input line 113 through a gantry support structure 112 and directed by one or more steering magnets in support 112 or gantry 114 or some combination to output port 116. In some embodiments, scanning magnets are included at the output port 116. Hereinafter the radiation source will be understood to mean the output port 116 unless otherwise clear from the context. Combining the effects of multiple beams (their intensities and shapes), the goal is to transmit high dose to the target region 192, and low dose to the tissue of the subject 190 outside the target region. During the operation of the system 100, the radiation source output port 116 rotates with gantry 114 around the support structure 112 and the subject 190 is positioned on a moveable couch 124 mounted on couch support 120, so that the beam is directed at the target region 192 from multiple directions. In the stationary global spatial coordinate system 130, the vertical dimension is indicated by a z axis, and the horizontal dimensions by an x axis transverse to the couch at a zero couch angle and a y axis oriented along the couch at zero couch angle as shown in FIG. 1A. This is related to the Digital Imaging and Communications in Medicine (DICOM) standard axes as given by Equation 1a through 1c.

$$X_{global} = X_{DICOM} \tag{1a}$$

$$Y_{global} = -Z_{DICOM} \tag{1b}$$

$$Z_{global} = -YX_{DICOM} \tag{1c}$$

The gantry rotates an angle θ 119 in the x-z plane about an axis of rotation considered to occur at the origin 131 of the z axis and parallel to the y axis. The couch 124 can be moved vertically and rotated an angle φ 123 in the x-y plane around the z axis.

According to various embodiments, a digital image projector 140 is fixedly or adjustably mounted to the gantry 114 in the vicinity of the radiation source output port 116. The light projected from the projector is not aligned with an axis of the beam 115 of radiation from the radiation source output port 116. The image projector is operated to illuminate an outer surface of the subject 190 to indicate a region where a beam 115 from the radiation source output port 116 will intersect that outer surface. This is advantageous because it provides feedback to the operator of the system that the subject is properly aligned to receive the desired total dose according to a treatment plan. In some embodiments, the system 100 includes a monitor chamber 132 to measure the direction and width of the beam from the output port 116. FIG. 1B shows some of the same components in a transverse x-z plane, as well as a non-coaxial light beam 148.

As illustrated in FIG. 1A, a computer system 150 is provided to determine the intensity and shape of the beam 115 from the source output port 116 for each of multiple beams at one or more gantry angles and one or more couch angles and one or more couch heights according to a treatment plan. The computer system 150 also transmits the appropriate parts of the determined information: to a controller 118 for the gantry and radiation source; and to a controller 122 for couch 124. The information is transmitted over one or more wired or wireless communication lines 152.

The computer system 150 includes an illumination module 142 to build an image to be projected by the digital image projector based at least in part on treatment plan data 152, so that when projected onto the surface of the subject 190 (called "skin" of the subject for convenience whether or not the subject is clothed), an operator can see where the radiation from the radiation source output port 116 will intersect the surface of the subject. Because the light beam 148 from the projector is not aligned with the axis of the beam 115 from the radiation source output port 116, the projector 140 is said to be non-coaxial with the radiation source 116. Thus, the digital image projector 140 and module 142 provide for skin illumination of radiation therapy treatment area using a non-coaxial digital projector.

Figure 8:
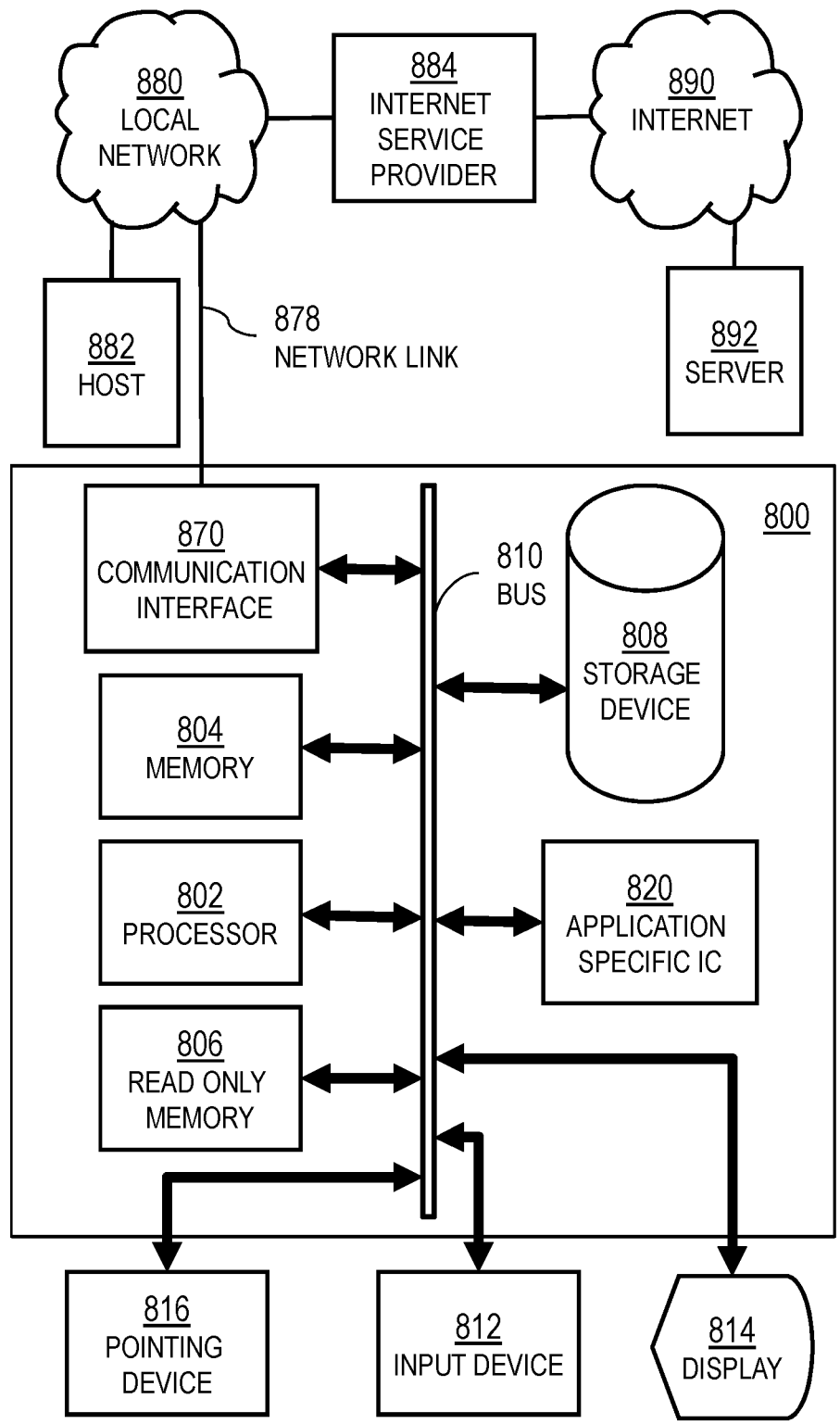
FIG. 8 is a block diagram that illustrates a computer system upon which an embodiment of the invention may be implemented.
Figure 9:
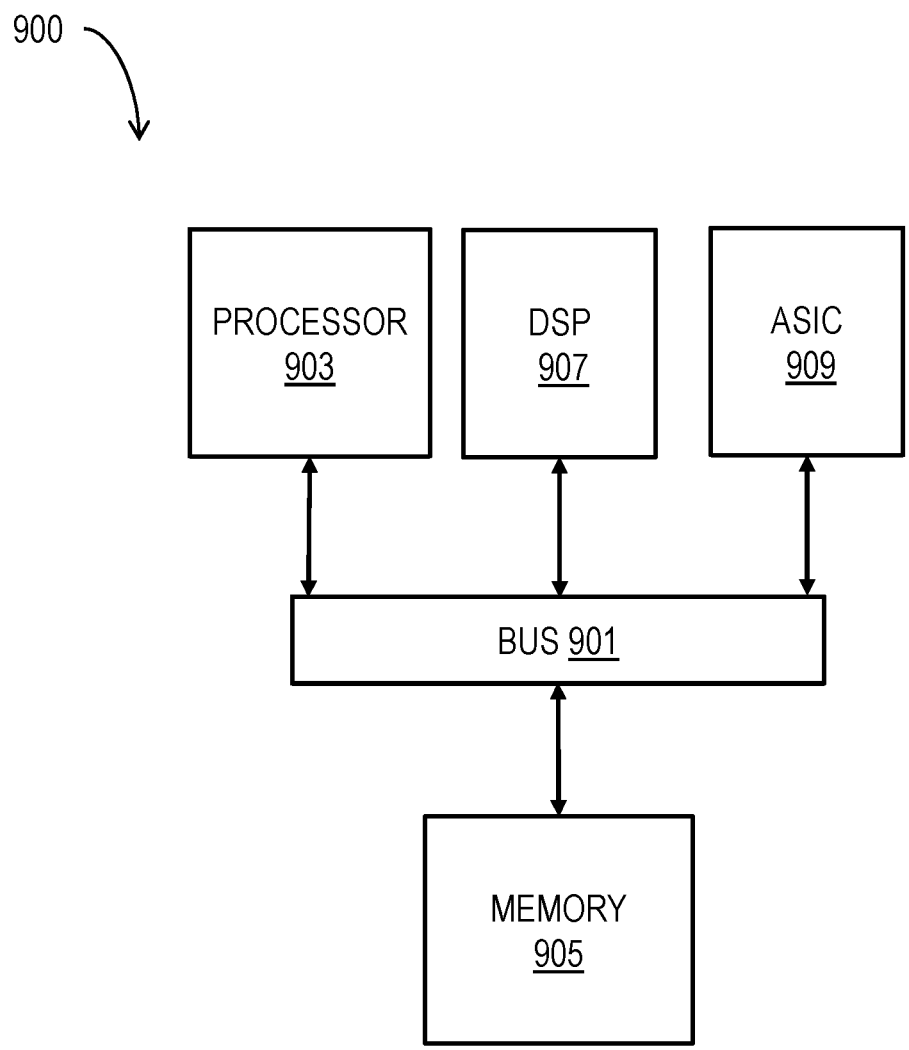
FIG. 9 illustrates a chip set upon which an embodiment of the invention may be implemented.

In various embodiments, the computer system 150 comprises one or more general purpose computer systems, as depicted in FIG. 8 or one or more chip sets as depicted in FIG. 9, and instructions to cause the computer or chip set to perform one or more steps of a method described below with reference to FIG. 6.

Although processes, equipment, and structures are depicted in FIG. 1A and FIG. 1B as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, all or part of module 142 may be performed by controller 118 for the gantry and radiation source or by controller 122 for the couch 190, or some combination.

A treatment plan is prepared for treating a subject, such as a human or animal patient or a surrogate such as an inanimate phantom or control object, and includes treatment plan data 152 that indicates information about the subject placement on the couch 124, the height and orientation angel φ of the couch, the outer surface of the subject at φ=0 in global coordinates, the target region at φ=0 in global coordinates, including an outer surface of the target region and a central point, called the isocenter. The isocenter is near or inside the target region; and, is aligned with the axis of rotation of the gantry and the axis of rotation of the couch. After treatment of the target region in the neighborhood of the isocenter, the couch can be moved horizontally and vertically or the gantry rotated, or some combination, so that a different target region inside the subject can be treated and a different point occupies the isocenter. The new locations of skin and target region can be obtained using the original values at φ=0 and operating on those values with a spatial transform for given rotation and vertical displacement of the couch.

Figure 2A:
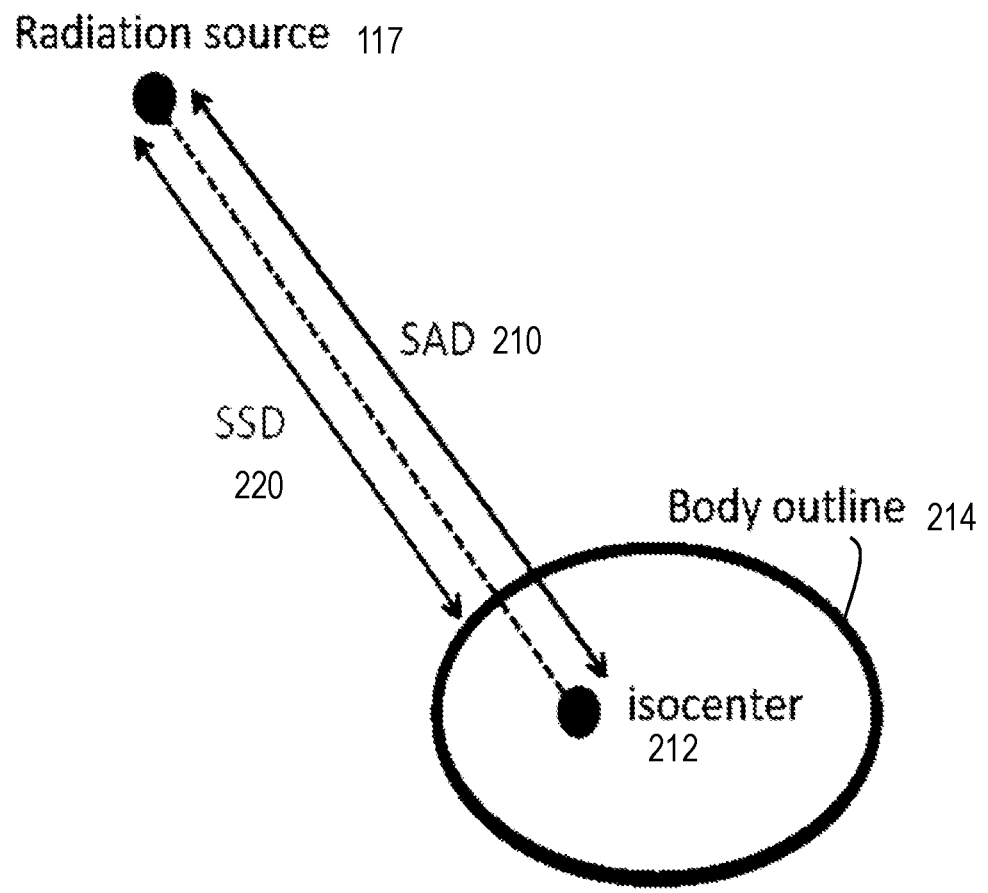
FIG. 2A through FIG. 2C are block diagrams that illustrates example parameters of the treatment plan that are utilized, according to an embodiment.
Figure 2B:
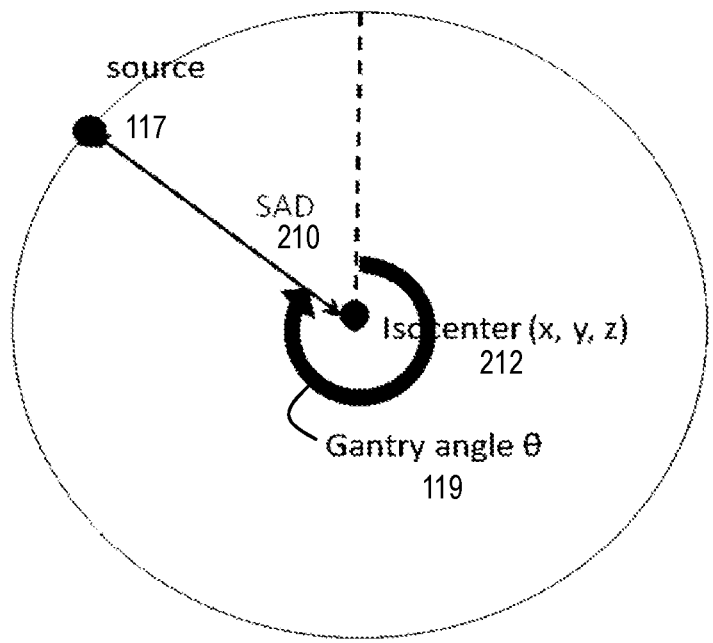
Figure 2C:
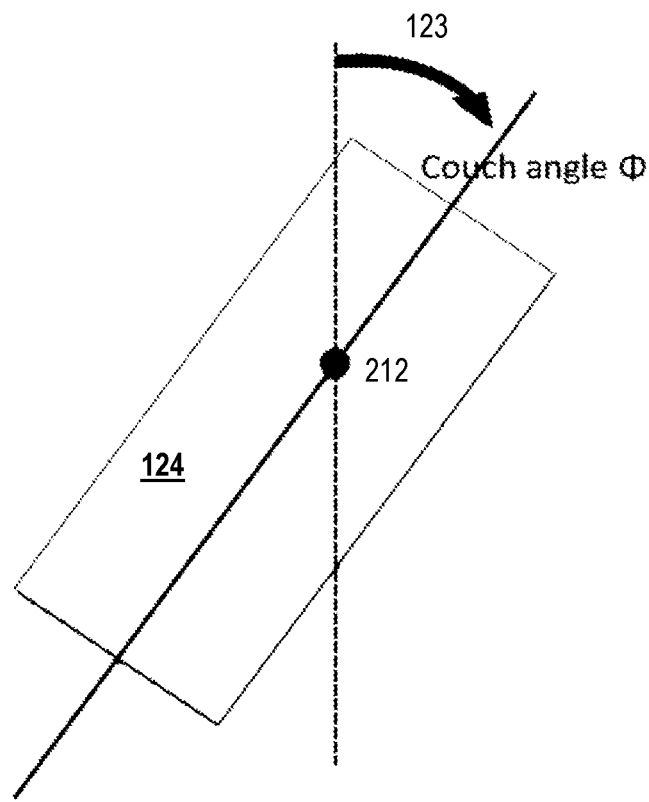

FIG. 2A through FIG. 2C are block diagrams that illustrates example parameters of the treatment plan that are utilized, according to an embodiment. FIG. 2A depicts example coordinates of the radiation source 117, and isocenter 212, along with the coordinates of the outer surface of the subject, called "body outline" 214. Although only two dimensions are depicted in FIG. 2A for the center beam of the radiation source, the treatment plan includes coordinates for other locations in the target region, called target volumes, hereinafter, and coordinates of the body outline in the third dimension perpendicular to the plane of FIG. 2A. The body outline 214 can be expressed in any manner known in the art, including an analytical function, or discrete points that can be interpolated with straight line segments or triangles or any other polygon. The distance from the radiation source origin 117 to the isocenter along the center beam (i.e., the beam axis) is designated source axis distance, SAD 210. The distance from the source origin 117 to the skin of the subject (called the source skin distance, SSD 220) can be computed from the SAD 210, the coordinates of the isocenter 212, and the coordinates of the body outline 214, as described in more detail below. FIG. 2B depicts the gantry angle θ, measured in this example clockwise relative to the radiation source pointing straight down (−z direction) in the z-x plane. FIG. 2C depicts the horizontal surface of the couch 124 in the x-y plane and the couch angle φ, measured in this example clockwise, looking in the −z direction, from the y axis that is parallel to the axis of rotation of the gantry.

Figure 3A:
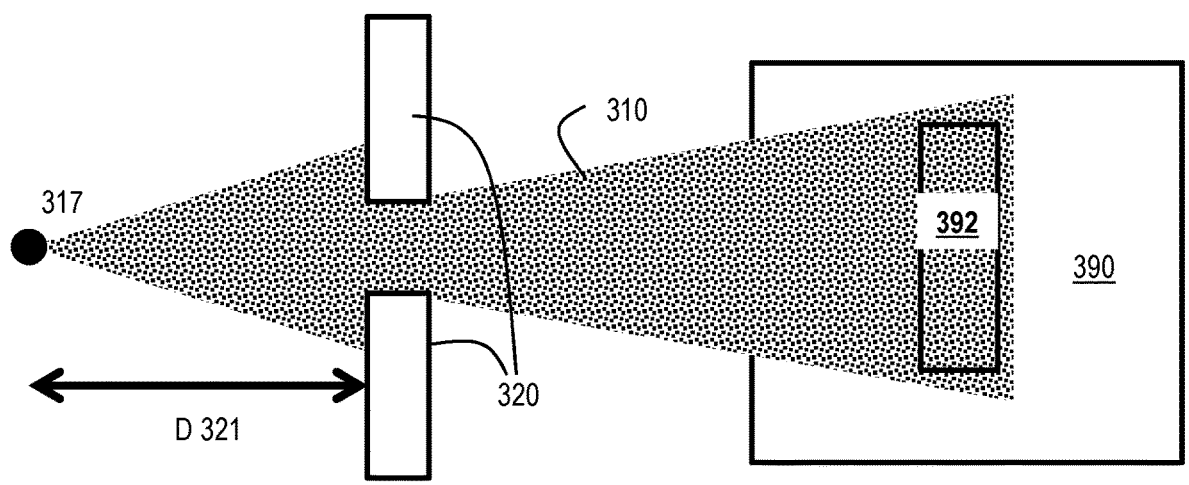
FIG. 3A is a block diagram that illustrates an example radiation source that produces a radiation beam shaped by an aperture in a collimator, used in some embodiments.
Figure 3B:
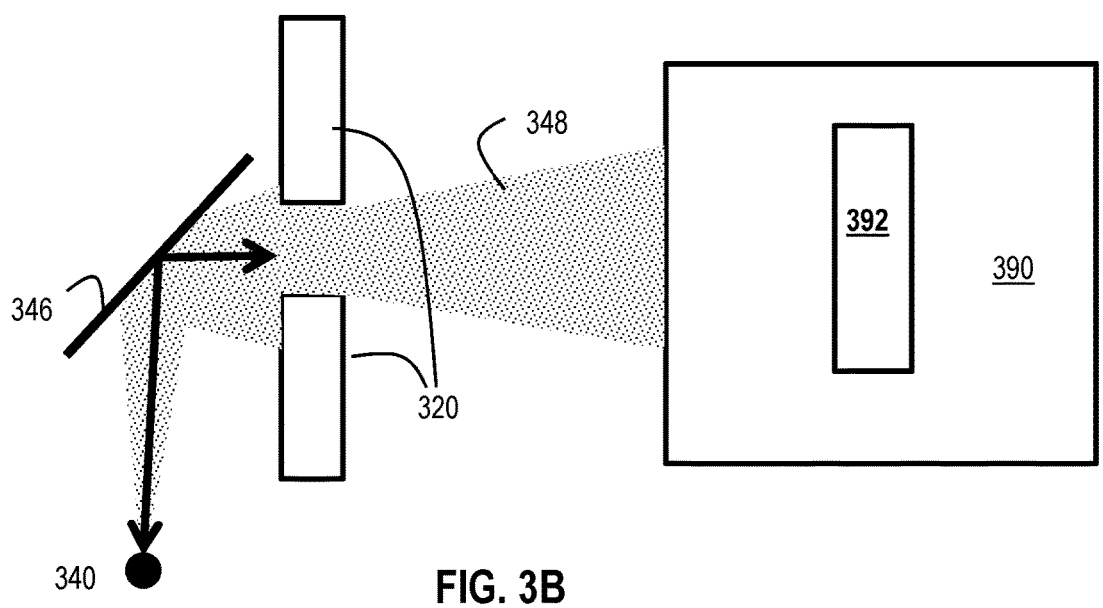
FIG. 3B is a block diagram that illustrates an example illumination technique that uses a co-axial path to illuminate the skin of a subject.

In some radiation therapy systems, the radiation is applied in a diverging beam from the point of the radiation source 117 and is shaped by a variable aperture, such as a multi-leaf collimator. FIG. 3A is a block diagram that illustrates an example radiation source that produces a radiation beam 310 shaped by an aperture in a collimator 320, used in some embodiments. The radiation is emitted from a point emitter 317, or a fan of scanning beams, a distance D 321 from the collimator and penetrates into the body of subject 390 to a target region 392 where the energy is dissipated. FIG. 3B is a block diagram that illustrates an example illumination technique that uses a co-axial path to illuminate the skin of the subject 390. A point emitter of light 340 and a mirror 346 are used to produce a new path with the same distance D 321 to the same aperture in the same collimator 320. As a result, the light beam 348 diverges like the radiation beam 310 and automatically illuminates the area of the skin of the body 390 that is penetrated by the radiation beam 310.

Figure 4A:
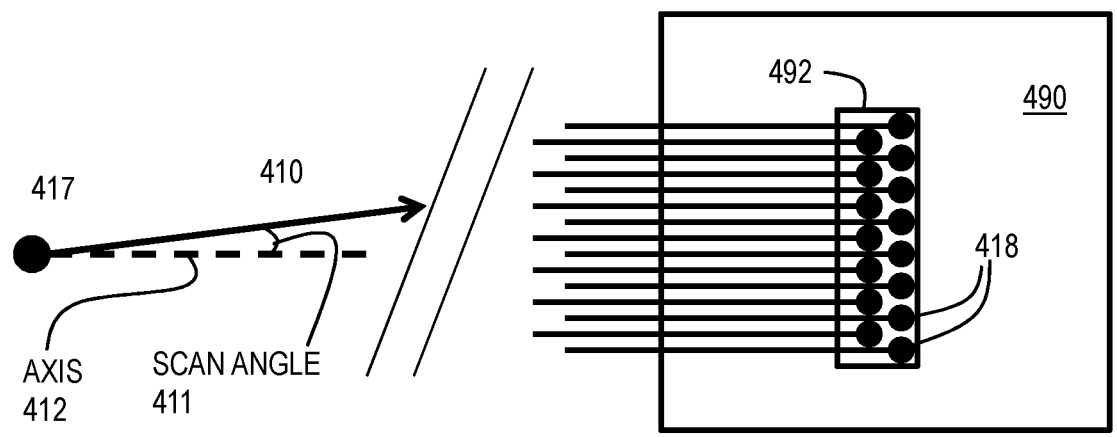
FIG. 4A is a block diagram that illustrates an example scanning pencil beam radiation source, used in many modern particle beam sources, according to some embodiments.

However, this method cannot be used if the radiation source is not configured to give access to the same aperture in the same collimator or to allow insertion of mirror 346 or does not use a collimator. Such is typically the case for scanning particle beam sources that do not even use a collimator 320. FIG. 4A is a block diagram that illustrates an example scanning pencil beam radiation source, used in many modern particle beam sources, according to some embodiments. At any instant, only a thin beam called a pencil beam is emitted from a source 417. Scanning components (e.g., magnets or optics, not shown) are used to point the pencil beam through any of a variety of small scan angles 411 around an axis 412 at the center of a fan of such beams over a short time, completing the fan in a time on the order of millisecond to seconds. For example, in experimental embodiments described below, the distance from the output port is about 230 cm, beam width is between 6 mm to 12 mm in air; and, it takes a few milliseconds to deliver one spot, a few seconds for one energy layer, and a few minutes for one beam. Each beam 410 penetrates the skin of a subject 490 to a target region 492 where the energy is largely absorbed at one subregion 418 called a target volume. As the pencil beam is scanned over multiple angles, the energy is primarily absorbed at multiple target volumes 418 at one depth within the subject. By using a pencil beam of a different energy, the beam energy is absorbed in a target volume at a different depth. In a short time, multiple target volumes that span the entire target region 492 are radiated. Because this radiation source does not use a collimator, a coaxial illumination scheme like that depicted in FIG. 3B is not appropriate; and, indeed, might not be possible.

Figure 4B:
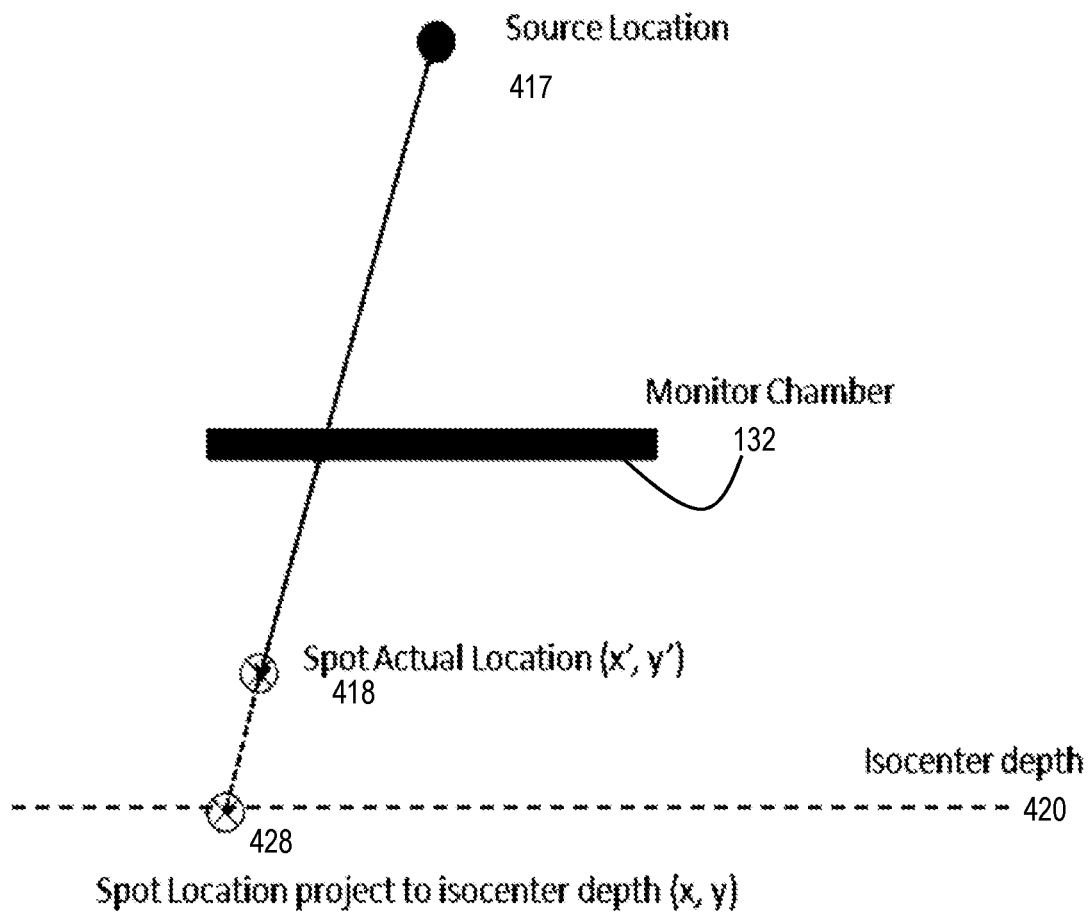
FIG. 4B is a block diagram that illustrates configuration of a radiation monitor chamber in a system, according to an embodiment.

FIG. 4B is a block diagram that illustrates configuration of a radiation monitor chamber 132 in a system, according to an embodiment. Monitor chamber 132 detects the intersection of the radiation beam 115 with the chamber and returns a 2D location in the beam eye view (BEV, also called the axial coordinate system) to compare to a value from a treatment plan (TPS). No matter what the x and y and z value is for the target volume 418 in actual 3D space inside the subject, the output from the monitor chamber system is always projected to isocenter depth 420 for monitoring purposes. The monitor chamber is calibrated to the x and y location 428 at isocenter depth 420.

Figure 5A:
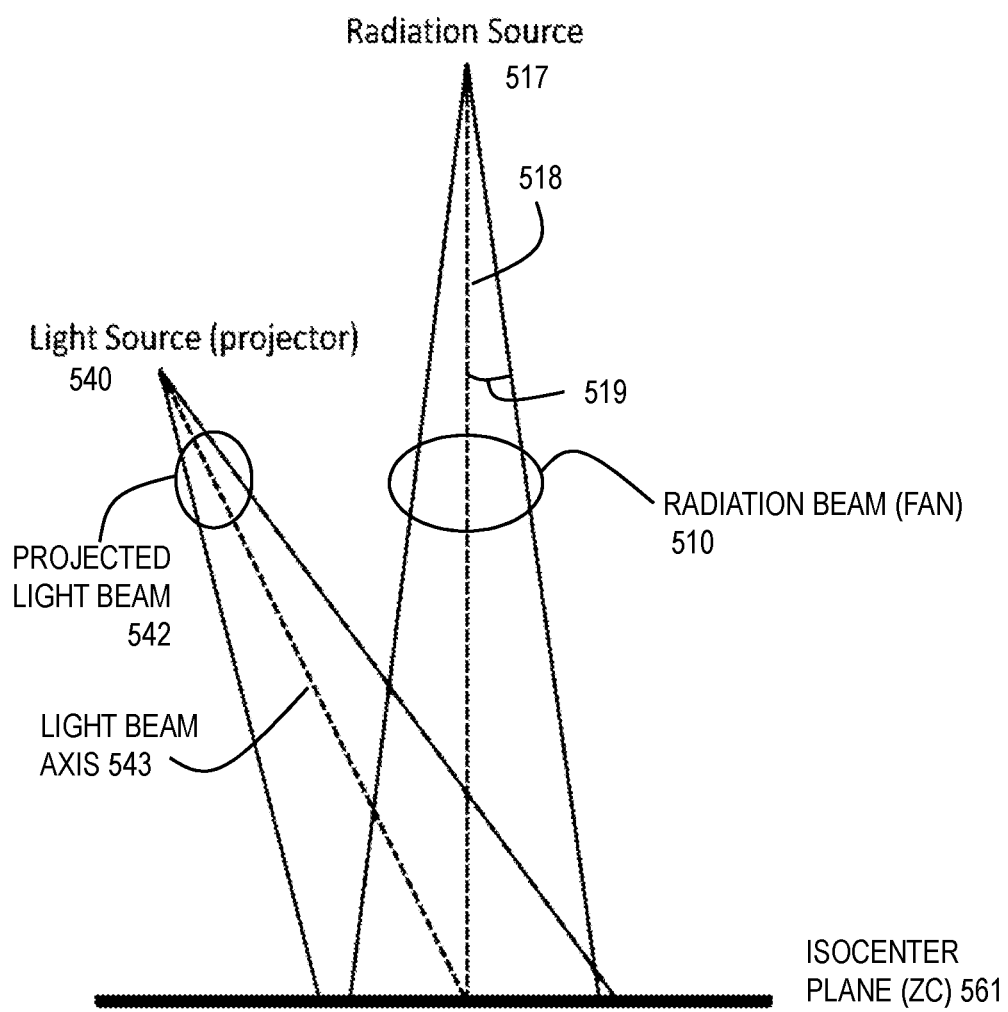
FIG. 5A is a block diagram that illustrates an example non-coaxial digital image projector used to illuminate a radiation therapy treatment region, according to an embodiment.

FIG. 5A is a block diagram that illustrates an example non-coaxial digital image projector used to illuminate a radiation therapy treatment region, according to an embodiment. The radiation source 517 produces a diverging beam 510, or fan of scanned pencil beams, with axis 518 and angle spread 519 directed to isocenter plane at distance ZC 561. A digital image projector having a light source 540 is displaced from the radiation source and projects a light beam 542. The image so projected is computed to illuminate spots on the skin of the subject that correspond to spots where the pencil beam fan or beam 510 from the radiation source will penetrate the skin of the subject. The illuminated spots appear as white spots on a black (light absent) background in the digital image computed. The axis 543 of the projected light beam is not aligned with the axis 518 of the radiation source 517; thus, the projected light beam 542 is not coaxial with the radiation beam 510. While the radiation from a beam of a certain energy is largely absorbed at target volume approximately on the isocenter plane (ZC) 561, or one or more parallel planes nearby (as depicted in FIG. 4), or some combination, the skin of the subject is, in general, not on or near the isocenter plane.

Figure 5B:
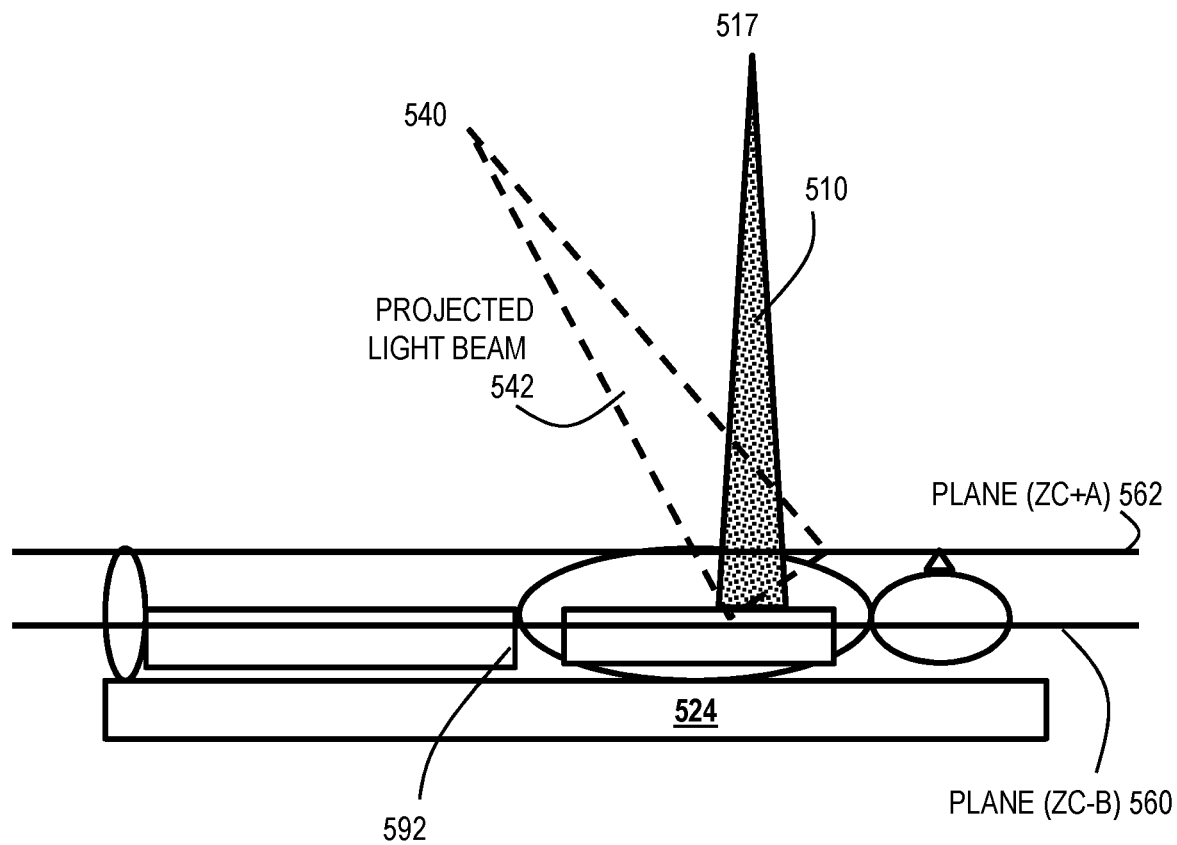
FIG. 5B is a block diagram that illustrates an example body outline with the skin of the subject not on the isocenter plane, according to an embodiment.

FIG. 5B is a block diagram that illustrates an example body outline 592 of a subject with the skin of the subject not on the isocenter plane, according to an embodiment. The subject lies on the couch 524 and the radiation beam 510 from source 517 is used to irradiate the target region at or near the isocenter on the isocenter plane. A source 540 of a projected light beam 542 is used to illuminate a region on the body outline 592 of the subject that includes the spots to be illuminated where the radiation beam 510 intersects the skin of the subject. A plane at or above the uppermost outline of the subject, e.g., plane ZC+A 562, and a plane at or below the isocenter plane, e.g., plane ZC−B 560, are selected to bracket the body outline 592 of the subject in the skin region to be illuminated.

Because the light beam 542 is not coaxial with the radiation beam 510, there is parallax that affects where a spot in a computed projector image ends up when projected on the skin of the subject, i.e., parallel lines in the computed projector image may not be parallel when projected onto the skin of the subject. FIG. 5C and FIG. 5D depict the difference between a computed reference image and the same image when projected on the skin of a subject, according to an embodiment. In this example the computed image is a square grid; and if it were projected from the position of the radiation source 517 perpendicular to the plane of the surface of the couch, it would appear relatively undistorted as in reference image 541 on plane Z, e.g., ZC+A 562. However, because the reference image is projected from an angle that is not perpendicular to the plane of the surface of the couch, the far edge is longer than the near edge, as in trapezoidal projected image 544 on the same plane. The same two images are depicted in FIG. 5D. Selecting corresponding points on the two images, a vector that indicates a perspective transform can be determined, as described in more detail below. Using multiple such reference points, e.g., the four corner vectors depicted, a perspective transform matrix is determined for the plane Z. According to various embodiments, the perspective transform matrix for each of multiple planes is used to build an illumination image that can be projected onto the skin of the subject to illuminate regions where the radiation beam intersects the skin of the subject.

2. Overview of Method

Figure 6:
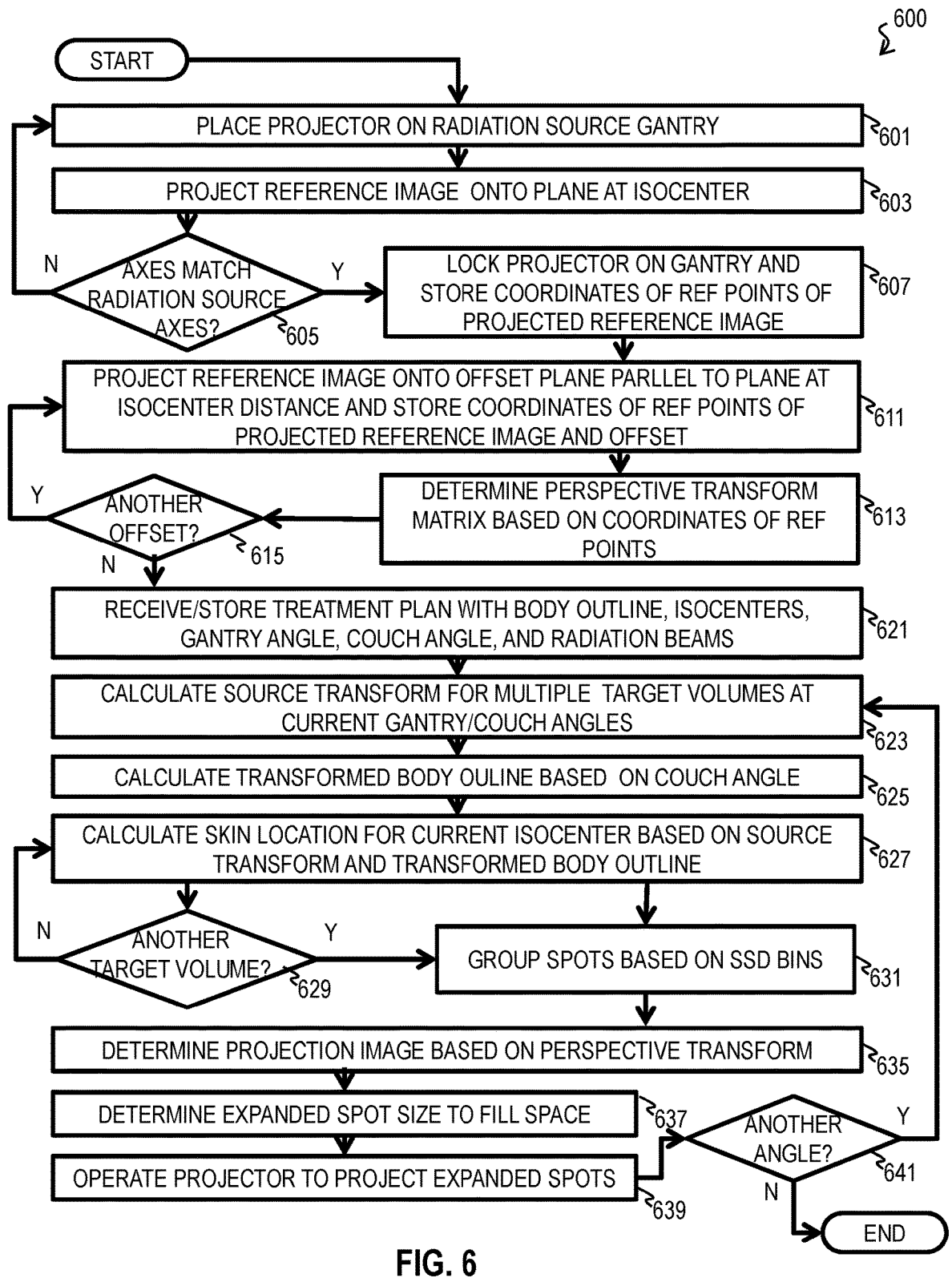
FIG. 6 is a flow diagram that illustrates an example method for skin illumination of radiation therapy treatment region using non-coaxial digital projector, according to an embodiment.

FIG. 6 is a flow diagram that illustrates an example method 600 for skin illumination of radiation therapy treatment region using a non-coaxial digital projector, according to an embodiment. Although steps are depicted in FIG. 6, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. For example, in some embodiments, the treatment plan received in step 623 is received before the calibration performed in steps 603 to 615.

In step 601, a digital image projector is placed on the gantry near the radiation source. The advantage of using a digital image projector is that an area on an arbitrarily shaped subject can be illuminated without the need for complex scanning optical couplers or any moving parts. The device is fixed, and the image to be projected is manipulated computationally to take care of the variations among different patients and different treatment plans and the differences in offset distance and pointing angles and rate of divergence from the radiation source. Any of a large number of commercially available digital image projectors can be used, such as portable projectors: C800S Projector from Shenzhen Cocar Electronic Technology Co. Ltd, of Shenzhen, China; KP-101-01 Pico micro Video Projector from AAXA Technologies of Irving, California; MP-CL1A from SONY Corporation of America, New York, New York; Minibeam LED Projector from LG Electronics America of Huntsville, Alabama; Pocket Projector PPX4350 from Royal PHILIPS of Eindhoven, Netherlands. Small devices are advantageous as providing less interference with the normal operation of the system 100.

Any manner of mounting may be used. It is advantageous to fix the projector so that the light beam from the digital projector will intersect the radiation beam at a range of distances where subjects are likely to be deposed on the couch, e.g., at distances from the isocenter plane in a range from about +/−25 centimeters (cm) covering a maximum radiation field size of about 30 cm by 40 cm on the isocenter plane. In some embodiments, the mounting is done with adjustable mounts, such as screws, that can be operated to slightly change position and orientation of the projector. In addition, if the projection lens pointing direction is adjustable after fixing the projector, that feature can be used to extend the range of distances. The calibration steps 603 to 615, described below, are advantageously repeated any time the device is replaced or re-pointed, or the isocenter plane changes substantially, or periodically to correct for any physical shifts or electronic drifts. It is preferable to calibrate the light field every time when replacing the projector. It is advantageous to calibrate periodically (daily or monthly or annually) to verify the calibration stays the same.

In step 603 a set of reference points with known global coordinates relative to the isocenter of the treatment plan, such as a square grid, is both: a) laid out physically on a first plane perpendicular to the radiation beam axis, e.g., onto a perpendicular plane at the isocenter distance, using global coordinates, and also b) projected onto the plane from the projector using projector coordinates scaled from the global coordinates. The scale factor, t, corrects for the maximum size in the projector image to correspond to the maximum size of the reference points laid out physically. The reference points in the global coordinates represent a fixed set of points projected from the radiation source and thus the reference grid expands with distance from the radiation source. For this reason, the set of reference points relative to the radiation source are called herein the axial reference points. The axial reference frame is also called the beam-eye's view (BEV). Step 603 is easily accomplished when the radiation source beam axis is directed downward in the vertical direction (e.g., gantry angle θ=0 degrees) by projecting the image onto the now perpendicular surface 125 of the couch 124. The couch surface 125 can be moved to the corresponding distance from the radiation source (e.g., the isocenter vertical coordinate ZC) or a screen can be positioned on the couch at the correct distance, in various embodiments. The set of axial reference points need not be a square grid but can be any set of four or more reference points for each of which the global coordinates relative to the isocenter are known. It is advantageous for the set of points selected to indicate both the x and y axes with the origin at the isocenter. If the isocenter is not known, e.g., because calibration is done before the treatment plan is provided, a plane near the expected isocenter, e.g., near center of the subject, is used as a surrogate isocenter plane. For example, the reference points are printed on the surface 125 of the couch 124 or on a screen or sheet of paper placed on or a known distance above the surface 125 of the couch 124. In some embodiments, the radiation source includes a light projector that projects reference points along the radiation beam, e.g., cross hairs at the radiation beam axis extending in the x and y axes directions and at one or more points on the periphery of the reference beam.

Figure 7A:
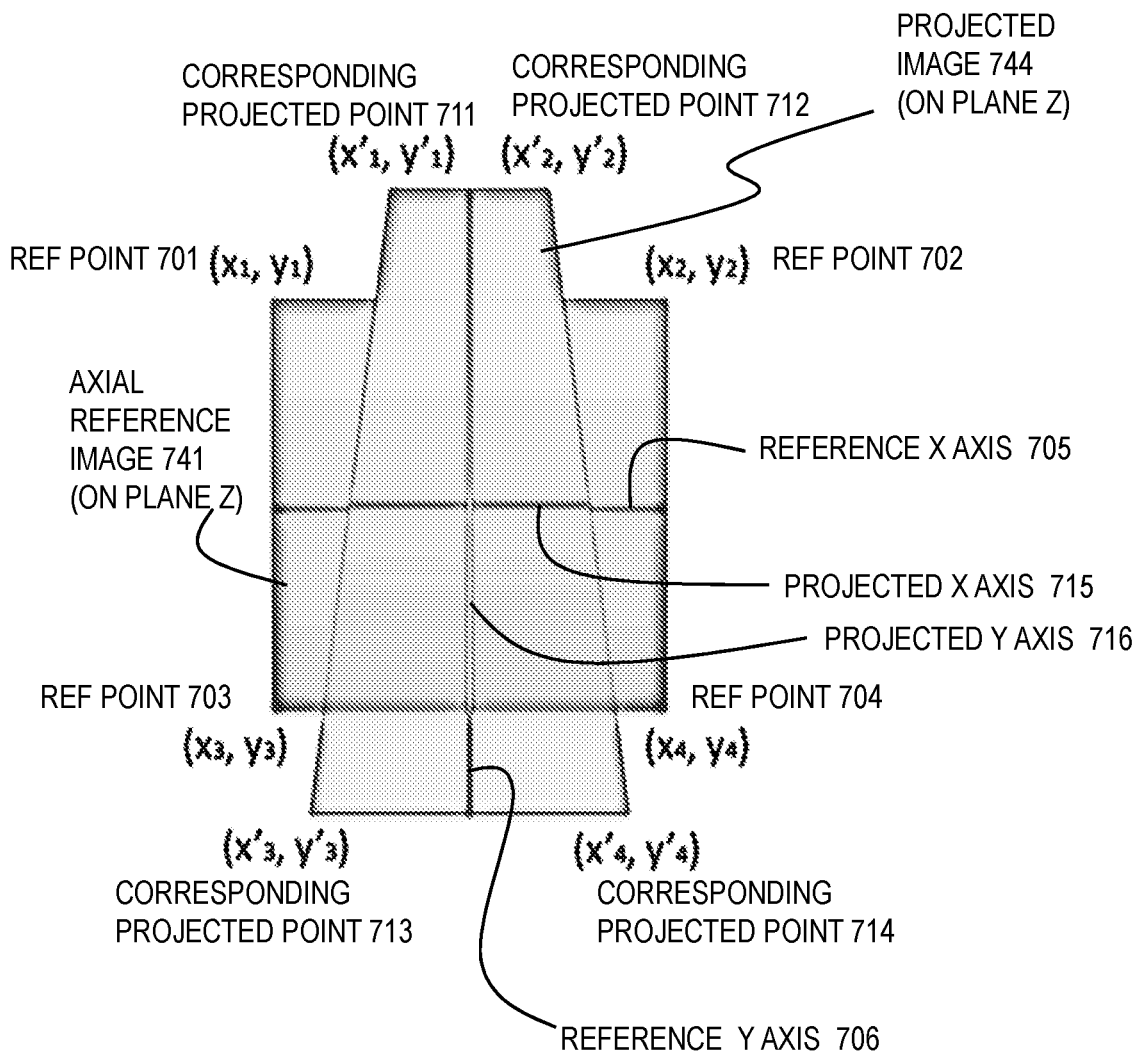
FIG. 7A is a block diagram that illustrates an example set of axial reference points physically located on a plane perpendicular to the radiation beam axis at distance Z in global coordinates and input to the digital image projector as projector image coordinates, and the resulting projected image 744 on the plane, according to an embodiment.

FIG. 7A is a block diagram that illustrates an example set of axial reference points as axial reference image 741 located on a plane perpendicular to the radiation beam axis at distance Z in global coordinates and input to the digital image projector with factor t as projector image coordinates, and the resulting projected image 744 on the plane, according to an embodiment. Every grid point on the grid can be used as a reference point, but for this example it is illustrative to consider four corner axial reference points on the grid 701, 702, 703, 704 with global coordinates (x1, y1), (x2, y2), (x3, y3) and (x4, y4), respectively. When the projector image of the same reference points is projected onto plane at distance Z, the corresponding points appear at the corners of a trapezoidal shape as projected reference points 711, 712, 713, and 714, respectively. Similarly, when the reference image of the x and y axes 705 and 706, respectively, are projected onto the first plane at distance Z, the corresponding axes are 715 and 716, respectively. It is advantageous to select the distance Z to be the distance of the isocenter plane ZC, because that is likely within a few tens of centimeters of the skin of the subject and the projector will be suitably aligned to project onto the skin of the subject. Also, the treatment plan is often specified relative to the isocenter. In some embodiments, all the target volumes are projected to one plane, as described in more detail below, and it is advantageous to make the calibration measurements with the axial reference points defined for that first plane. Because the target volumes are defined relative to the isocenter, it is advantageous to use the isocenter plane as the one plane for projecting all target volumes, and therefore advantageous to make the isocenter plane, or the surrogate isocenter plane, the first plane. If the isocenter is not known precisely, a vertical distance near an expected isocenter usefully serves as the first plane in some embodiments.

In step 605, it is determined whether the axes of the two images are aligned. For example, it is determined whether projected x axis 715 coincides with axial reference x axis 705 and projected y axis 716 coincides with axial reference y axis 706. If not, control passes back to step 601 to adjust the placement of the digital projector 140. How to adjust the projector would be readily determined by experimentation, depending on the method of mounting, such as drilling new holes in the gantry to attach an articulated platform with tightening means, using two-sided tape, using a bracket with adjustment screws, among others, or some combination. If both axes are aligned, then control passes to step 607.

In step 607, the projector and pointing lens, if any, is fixed for the duration of the calibration and subsequent one or more treatments. Also, during step 607, data based on the projection on plane Z is recorded for later use. For example, the global coordinates (x1, y1), (x2,y2),(x3,y3) and (x4,y4) of the corner axial reference points 701, 702, 703 and 704, respectively, are determined and recorded; and, the global coordinates (x'1, y'1), (x'2,y'2), (x'3,y'3) and (x'4,y'4) of the corresponding corner projected reference points 711, 712, 713 and 714, respectively, are determined and recorded. In some embodiments, the coordinates are read off a printed grid on a template laid on the couch. In some embodiments the points are digitized with a manual pointer. In some embodiments the projected image on top of the printed reference points is digitally photographed and the reference points determined automatically from the digitized photo.

In some embodiments, the global coordinates of the projected reference points and global coordinates of the axial reference points are used to generate a perspective transform matrix for the current plane at height Z, e.g., at isocenter height ZC, for the first plane. A perspective transform matrix $M_i$ for the ith plane is defined by Equation 2a and 2b.

$$\begin{bmatrix} t_i x'_i \\ t_i y'_i \\ t_i \end{bmatrix} = M_i \begin{bmatrix} x_i \\ y_i \\ 1 \end{bmatrix} \quad (2a)$$

where each $$M_i = \begin{pmatrix} a_1 & a_2 & b_1 \\ a_3 & a_4 & b_2 \\ c_1 & c_2 & t \end{pmatrix} \quad (2b)$$

The index i indicates one plane of a set of I planes, i=1 to I, each at a different height, e.g., Zi. Since this is a two-dimensional transform, the position vector includes only the x value, the y value and a scale factor $t_i$. Thus, one unit of x and y in the axial reference frame on plane at height Zi goes to $t_i$ units in the projector frame. The perspective transform matrix $M_i$ has elements (each with subscript i understood and removed for simplicity) that represent rotation ($a_1$, $a_2$, $a_3$, $a_4$), translation ($b_1$, $b_2$) and expansion/contraction changes ($c_1$, $c_2$) within the plane, and scale factor t to convert to the projector frame which is constant for the current plane. The measured positions of the four reference points, each with an x value and a y value, provides 8 values to solve for the 8 unknowns $a_1$, $a_2$, $a_3$, $a_4$, $b_1$, $b_2$, $c_1$, $c_2$. The perspective transform matrix for the first plane is entered into a perspective transform matrix table accessible by plane identifier i or by plane z coordinate Zi.

In step 611, the projected grid is compared to the axial reference grid at a different plane parallel to, and offset vertically from the first plane by ΔZi, where a change upward is positive. The axial reference point coordinates are scaled to the offset plane by the factor f given in Equation 2c.

$$f = \{(Z_s - Zi) - \Delta Zi\}/(Z_s - Zi) \quad (2c)$$

where Zs is the height of the radiation source, because the axial reference points get closer together as the plane moves upward toward the radiation source. When the first plane is the isocenter plane, i.e., when Z=ZC, then Zs-Z=Zs-ZC=SAD and the factor f=(SAD-ΔZ)/SAD. The reference image is then projected from the digital image projector to the new plane, and the relative global coordinates of the projected reference points are measured.

In step 613, the perspective transform matrix M on the new plane is computed using Equations 2a through 2c based on the measured coordinates of the projected reference points on the new plane and the scaled coordinates of the axial reference points on the new plane. The perspective transform matrix for the new plane is entered into the perspective transform matrix table.

Figure 7B:
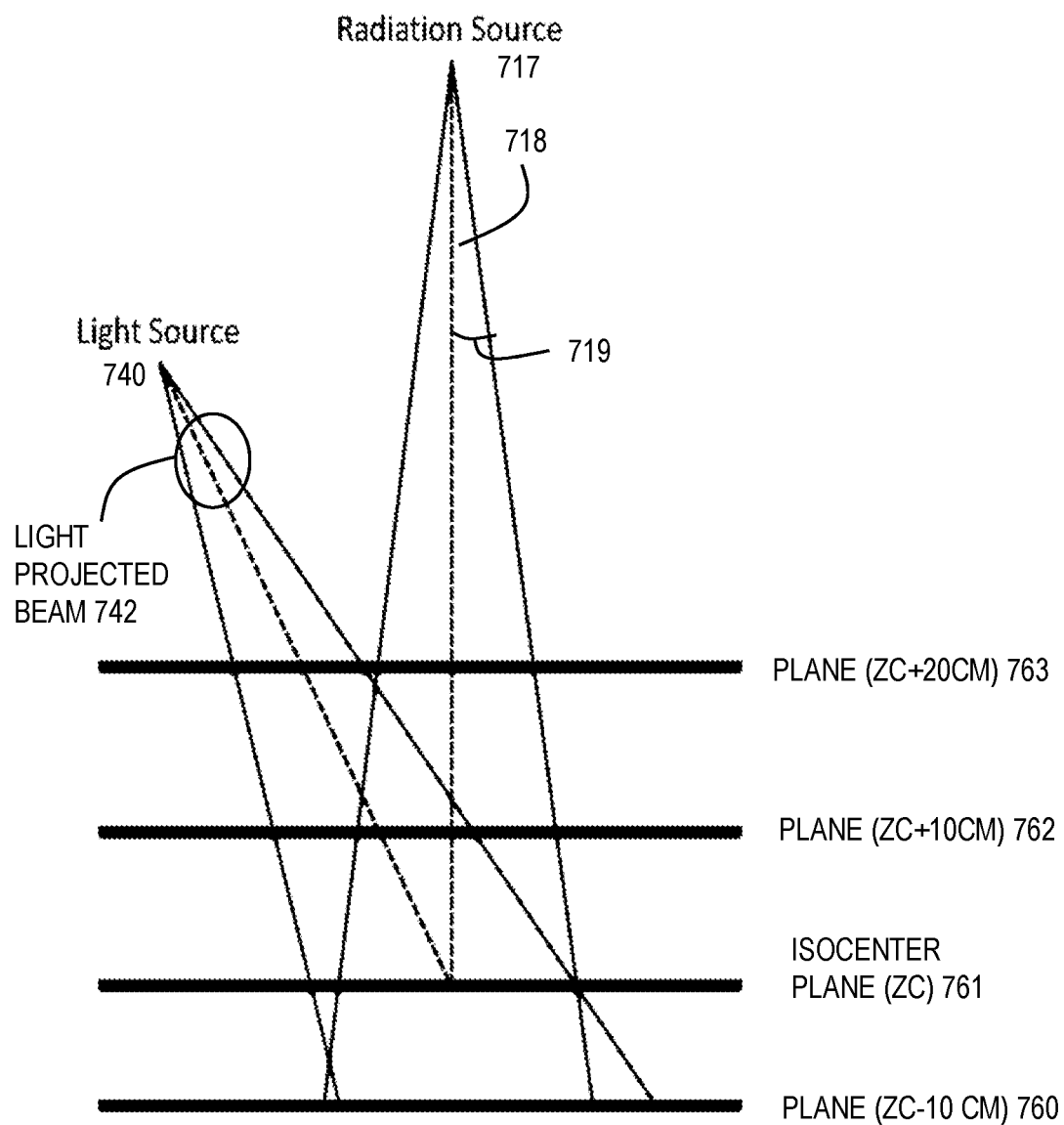
FIG. 7B is a block diagram that illustrates an example calibration for a radiation beam fan and light projected beam at four planes perpendicular to the radiation beam axis, according to an embodiment.

In step 615, it is determined whether there is another offset plane on which to determine a perspective transform matrix. If so, control passes back to step 611; otherwise, control passes to step 621. FIG. 7B is a block diagram that illustrates an example calibration for a radiation beam fan and light projected beam 742 at four planes perpendicular to the radiation beam axis, according to an embodiment. The light projected beam 742 emanates from the light source 740. The radiation beam fan emanates from radiations source 717 with beam axis 718 and angular spread 719. In this example embodiment, the first plane is at the isocenter plane (SAD, Z1=ZC) and the offset planes are at relative vertical distances ΔZ0=−10 centimeters (cm) (SAD+10), ΔZ2=+10 cm (SAD−10), and ΔZ3=+20 cm (SAD−20) corresponding to planes 761, 760, 762 and 763, respectively. In other embodiments, other values of ΔZi are used. It is advantageous for the spacing ΔZi of the Zi to be commensurate with the noticeable changes in the horizontal positions of projected spots, e.g., ΔZi on the order of 1 to 10 cm. The number I of different planes is then selected to span the range of skin heights on the area of the body outline where an image is to be projected.

In step 621 the treatment plan is received that indicates, at least, a gantry angle, a couch angle, and global coordinates or beam-eye view (BEV) coordinates for isocenter, for target volumes in vicinity of isocenter, and for body outline at couch angle φ=0. The gantry angle θ determines a source transformation; and, the couch angle φ determines a body outline transformation.

In step 623, a source transform is determined to transform treatment plan values for SAD and gantry angle θ and global coordinates ($x_{iso}$, $y_{iso}$, $z_{iso}$) for the isocenter to global coordinates for the source (called source coordinates indicated by $x_{source}$, $y_{source}$, $z_{source}$. At a non-zero value of 0, the coordinate systems are rotated as depicted in FIG. 2B.

$$z_{source} = z_{iso} + SAD \cos \theta \quad (3a)$$

$$x_{source} = x_{iso} + SAD \sin \theta \quad (3b)$$

$$y_{source} = y_{iso} \quad (3c)$$

In step 625, a body outline transform is determined to transform treatment plan coordinates ($x_{body}$, $y_{body}$, $z_{body}$) for the body outline at zero couch angle (φ=0) to global coordinates (called new body coordinates indicated by $x_{new\_body}$, $y_{new\_body}$, $z_{new\_body}$) at a, possibly, non-zero value of p. The global coordinates are rotated as depicted in FIG. 2C. A fourth vector element refers to scale and because there is no scale change after the rotation, the fourth element of the vector remains 1.

$$\begin{bmatrix} x_{new\_body} \\ y_{new\_body} \\ z_{new\_body} \\ 1 \end{bmatrix} = \begin{bmatrix} \cos\varphi & \sin\varphi & 0 & 0 \\ -\sin\varphi & \cos\varphi & 0 & 0 \\ 0 & 0 & 1 & 0 \\ 0 & 0 & 0 & 1 \end{bmatrix} \cdot \begin{bmatrix} x_{body} \\ y_{body} \\ z_{body} \\ 1 \end{bmatrix} \quad (4)$$

In step 627, the source to skin distance (SSD) and BEV perpendicular x,y coordinate location is calculated for the next target volume from the treatment plan based on the transformed source and transformed body outline (new body). In general, a treatment plan is made up of one or more target volumes on each of one or more planes perpendicular to the radiation beam axis at the current gantry angle as depicted in FIG. 4. FIG. 7C is a block diagram that illustrates example multiple target volumes 788 from a treatment plan in a beam eye view (BEV), according to an embodiment. The target volumes are in target region 792 of subject 790. The next target volume 788 indicated by 3D coordinates are computationally projected as 2D spots onto a single plane, e.g., a plane perpendicular to the radiation beam axis at a distance corresponding to the first plane of the calibration procedure or the isocenter plane. FIG. 7D is a block diagram that illustrates example spots 772 on the isocenter plane which correspond to the target volumes 788 of FIG. 7C, according to an embodiment. This projection is convenient because spot location is monitored by the monitor chamber 132 during irradiation. A monitor chamber 132 controller returns 2D location to compare to the value from the treatment plan from the treatment planning system (TPS). No matter what the x and y value is for spot at actual 3D space, it is always projected to isocenter depth for monitoring purposes. The monitor chamber 132 controller is calibrated to the x and y location at isocenter depth in the BEV coordinates. The set of spots 772 on the single plane is called a spot map and each such 2D spot has coordinates ($x_{spot\_map}$, $y_{iso}$, $z_{spot\_map}$). The spot map in 3D is rotated with gantry angle. One knows the spot position on 2D plane perpendicular to beam axis at isocenter depth; so, when the gantry rotates, the plane also rotates. Then each target volume is rotated with the body outline as a 3D spot with coordinates ($x_{3D\_spot}$, $x_{3D\_spot}$, $x_{3D\_spot}$). For example, for a spot map on the isocenter plane, the coordinates relative to the body outline are given by Equation 5.

$$\begin{bmatrix} x_{3D\_spot} \\ y_{3D\_spot} \\ z_{3D\_spot} \\ 1 \end{bmatrix} = \begin{bmatrix} 1 & 0 & 0 & 0 \\ 0 & \cos\varphi & -\sin\varphi & 0 \\ 0 & \sin\varphi & \cos\varphi & 0 \\ 0 & 0 & 0 & 1 \end{bmatrix} \cdot \begin{bmatrix} x_{spot\_map} \\ y_{iso} \\ z_{spot\_map} \\ 1 \end{bmatrix} \quad (5)$$

The surface point for each target volume is the intersection of the body outline with the line connecting source to the rotated spot_map, e.g., ($x_{3D\_spot}$, $x_{3D\_spot}$, $x_{3D\_spot}$) for the target volume. This intersection can be computed any number of ways in various embodiments. In an example embodiment, it is determined using Equation 6

Surface Point=arg min{distance(Body Outline−3D spot)+distance(Source−Body Outline)} (6)

where arg min indicates the argument of all possible Body Outline points that gives the minimum sum of those two distances, i.e., that minimizes the sum of the distance from the source to the surface point added to the distance from the surface point to the rotated spot map. Then the surface to skin distance (SSD) distance is computed as given by Equation 7, and associated with the surface point and the corresponding spot 772 on the spot map.

SSDspot=distance(Source−Surface Point) (7)

In step 629, it is determined if there is another target volume in the treatment plan. If so control passes back to step 627 and the process repeated to produce the next surface point and associated SSD for the next target volume. If all target volumes have been processed, control passes to step 631.

Figure 7F:
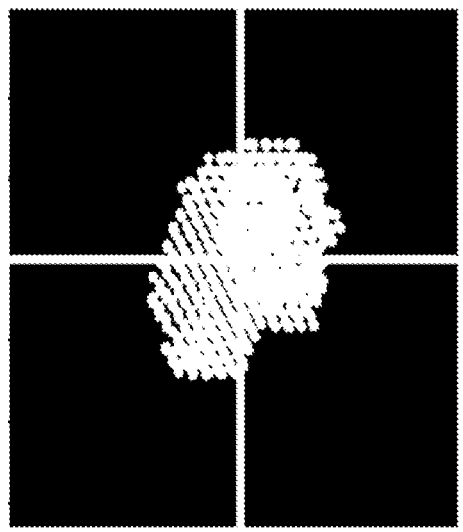
FIG. 7F is an image that illustrates an example surface point map for all target volumes in the view of the radiation beam, according to an embodiment.

In step 631, the surface points (or, more conveniently, the spot map spots 772) are grouped by the associated SSD values. This is done because the perspective matrix to use with the digital image projector depends on the SSD which gives the distance to the skin surface where the image is displayed. It is advantageous that the SSD bins should straddle the planes used to construct the perspective transform table, e.g., SSD bin i (SSDi) extend from Zi−ΔZ(i−1)/2 to Zi+ΔZi/2. FIG. 7E is a set of plots that illustrate example spots 772 on the spot map grouped by SSD values, according to an embodiment. The spots 772a in plot 770a shows the horizontal locations on the single perpendicular plane (e.g., the isocenter plane) of the spots 772 associated with surface points at a first SSD range bin, e.g., 1.00 to 1.01 meters. The spots 772b in plot 770b shows the horizontal locations on the single perpendicular plane (e.g., the isocenter plane) of the spots associated with surface points at a second SSD range bin, e.g., 1.01 to 1.02 meters. The spots 772c in plot 770c show the horizontal locations on the single perpendicular plane (e.g., the isocenter plane) of the spots associated with surface points at a last SSD range bin, e.g., 1.11 to 1.12 meters. FIG. 7F is an image that illustrates an example spot map (or, in some embodiments a surface point map) for all target volumes to be irradiated by the radiation beam at the current gantry and couch angle, according to an embodiment. Each spot has an associated SSDi.

In step 635, an image to input to the digital image projector, called a Projector image, is determined. For each range bin of SSD values, the perspective transform matrix Mi appropriate for the range bin from the lookup table is applied to indicate the coordinates in the projector image, indicated ($x_{proj}$, $y_{proj}$) corresponding to each Surface Point in the global coordinates, as given by Equation 7a and Equation 7b.

Projector Image($x_{proj}$,$y_{proj}$)=Surface Point at SSD$_i$
($M_{11}\cdot x+M_{12}\cdot y+M_{13}, M_{21}\cdot x+M_{22}\cdot y+M_{23}$) (7a)

Where $M_{jk}$ indicates the matrix element at row j and column k for the corresponding perspective transform matrix Mi. Then the points are collected for all the SSD bins to form the completed Projector image.

Projector Image=$\Sigma_{i=0}^{I}$Surface Point at SSD$_i$ (7b)

Figure 7G:
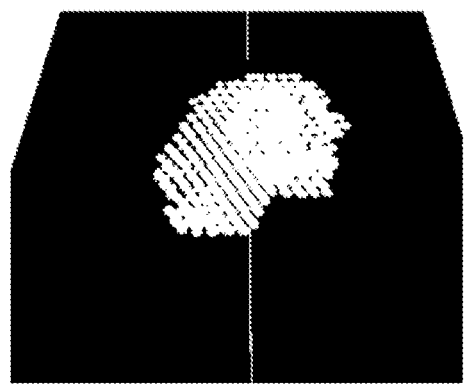
FIG. 7G is an image that illustrates an example Projector image for all target volumes in the view of the radiation beam, according to an embodiment.

In some embodiments, the x and y coordinates of the Surface Points are essentially the same as the x and y values of the 3D spots, so the 3D spots are used instead of the surface points in Equation 7a and 7b. FIG. 7G is an image that illustrates an example Projector Image for all target volumes in the view of the radiation beam, according to an embodiment.

Figure 7H:
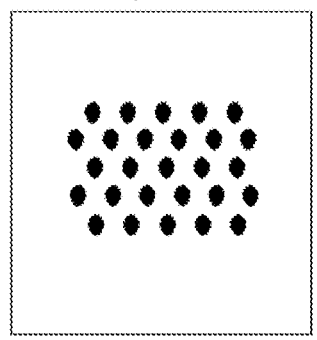
FIG. 7H is a pair of images that illustrates an example filling of spaces between locations of surface point for all target volumes in the view of the radiation beam, according to an embodiment.
Figure 7H:
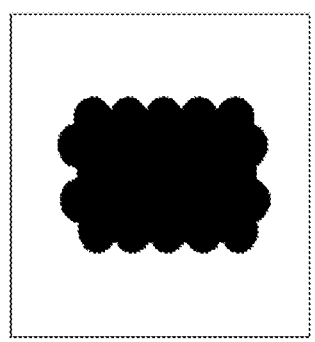

In step 637, the location of each projector image point, e.g., a nearest pixel location for the point, is surrounded by an illuminated spot sufficient to at least partially fill the spaces between the locations to produce a Spot-expanded Projector Image. Any method can be used to surround the pixels. For example, in some embodiments, the distances between projector image point pixels are accumulated and a maximum determined. The area around each pixel is expanded, e.g., using an image processing dilation command, by half the maximum distance. In some embodiments a histogram of pixel spacing is accumulated and a dilation scale is determined based on a property of the histogram, such as the mean value, median value, a largest mode value, a $75^{th}$ percentile value or some other percentile value; and, the area around each pixel is expanded, e.g., using an image processing dilation command, by half the dilation scale distance. FIG. 7H is a pair of images 774 and 776 that illustrates an example filling of spaces between locations of surface point for all target volumes in the view of the radiation beam, according to an embodiment. Image 774 indicates the pixel locations of surface points in the Projector Image and image 776 indicates the at least partially filled illumination areas in a Spot-expanded Projector Image.

In step 639, the digital image projector is operated to project the Spot-expanded Projector Image onto the subject. The radiation therapy clinician then uses the projected image to verify the treatment plan for the current subject and determine whether or not to operate the radiation source with the subject in place.

In step 641, it is determined whether there is another couch angel for the current gantry angle, or another gantry angle at which to operate the radiation beam in the treatment plan. If so, control passes back to step 623 and following steps to transform the coordinates for the source and body outline and compute a new Spot-expanded Projector Image. If not, then the process ends.

3. Computational Hardware Overview

FIG. 8 is a block diagram that illustrates a computer system 800 upon which an embodiment of the invention may be implemented. Computer system 800 includes a communication mechanism such as a bus 810 for passing information between other internal and external components of the computer system 800. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 800, or a portion thereof, constitutes a means for performing one or more steps of one or more methods described herein.

A sequence of binary digits constitutes digital data that is used to represent a number or code for a character. A bus 810 includes many parallel conductors of information so that information is transferred quickly among devices coupled to the bus 810. One or more processors 802 for processing information are coupled with the bus 810. A processor 802 performs a set of operations on information. The set of operations include bringing information in from the bus 810 and placing information on the bus 810. The set of operations also typically include comparing two or more units of information, shifting positions of units of information, and combining two or more units of information, such as by addition or multiplication. A sequence of operations to be executed by the processor 802 constitutes computer instructions.

Computer system 800 also includes a memory 804 coupled to bus 810. The memory 804, such as a random access memory (RAM) or other dynamic storage device, stores information including computer instructions. Dynamic memory allows information stored therein to be changed by the computer system 800. RAM allows a unit of information stored at a location called a memory address to be stored and retrieved independently of information at neighboring addresses. The memory 804 is also used by the processor 802 to store temporary values during execution of computer instructions. The computer system 800 also includes a read only memory (ROM) 806 or other static storage device coupled to the bus 810 for storing static information, including instructions, that is not changed by the computer system 800. Also coupled to bus 810 is a non-volatile (persistent) storage device 808, such as a magnetic disk or optical disk, for storing information, including instructions, that persists even when the computer system 800 is turned off or otherwise loses power.

Information, including instructions, is provided to the bus 810 for use by the processor from an external input device 812, such as a keyboard containing alphanumeric keys operated by a human user, or a sensor. A sensor detects conditions in its vicinity and transforms those detections into signals compatible with the signals used to represent information in computer system 800. Other external devices coupled to bus 810, used primarily for interacting with humans, include a display device 814, such as a cathode ray tube (CRT) or a liquid crystal display (LCD), for presenting images, and a pointing device 816, such as a mouse or a trackball or cursor direction keys, for controlling a position of a small cursor image presented on the display 814 and issuing commands associated with graphical elements presented on the display 814.

In the illustrated embodiment, special purpose hardware, such as an application specific integrated circuit (IC) 820, is coupled to bus 810. The special purpose hardware is configured to perform operations not performed by processor 802 quickly enough for special purposes. Examples of application specific ICs include graphics accelerator cards for generating images for display 814, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 800 also includes one or more instances of a communications interface 870 coupled to bus 810. Communication interface 870 provides a two-way communication coupling to a variety of external devices that operate with their own processors, such as printers, scanners and external disks. In general, the coupling is with a network link 878 that is connected to a local network 880 to which a variety of external devices with their own processors are connected. For example, communication interface 870 may be a parallel port or a serial port or a universal serial bus (USB) port on a personal computer. In some embodiments, communications interface 870 is an integrated services digital network (ISDN) card or a digital subscriber line (DSL) card or a telephone modem that provides an information communication connection to a corresponding type of telephone line. In some embodiments, a communication interface 870 is a cable modem that converts signals on bus 810 into signals for a communication connection over a coaxial cable or into optical signals for a communication connection over a fiber optic cable. As another example, communications interface 870 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 870 sends and receives electrical, acoustic or electromagnetic signals, including infrared and optical signals, which carry information streams, such as digital data.

The term computer-readable medium is used herein to refer to any medium that participates in providing information to processor 802, including instructions for execution. Such a medium may take many forms, including, but not limited to, non-volatile media, volatile media and transmission media. Non-volatile media include, for example, optical or magnetic disks, such as storage device 808. Volatile media include, for example, dynamic memory 804. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 802, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 802, except for carrier waves and other signals.

Logic encoded in one or more tangible media includes one or both of processor instructions on a computer-readable storage media and special purpose hardware, such as ASIC 820.

Network link 878 typically provides information communication through one or more networks to other devices that use or process the information. For example, network link 878 may provide a connection through local network 880 to a host computer 882 or to equipment 884 operated by an Internet Service Provider (ISP). ISP equipment 884 in turn provides data communication services through the public, world-wide packet-switching communication network of networks now commonly referred to as the Internet 890. A computer called a server 892 connected to the Internet provides a service in response to information received over the Internet. For example, server 892 provides information representing video data for presentation at display 814.

The invention is related to the use of computer system 800 for implementing the techniques described herein. According to one embodiment of the invention, those techniques are performed by computer system 800 in response to processor 802 executing one or more sequences of one or more instructions contained in memory 804. Such instructions, also called software and program code, may be read into memory 804 from another computer-readable medium such as storage device 808. Execution of the sequences of instructions contained in memory 804 causes processor 802 to perform the method steps described herein. In alternative embodiments, hardware, such as application specific integrated circuit 820, may be used in place of or in combination with software to implement the invention. Thus, embodiments of the invention are not limited to any specific combination of hardware and software.

The signals transmitted over network link 878 and other networks through communications interface 870, carry information to and from computer system 800. Computer system 800 can send and receive information, including program code, through the networks 880, 890 among others, through network link 878 and communications interface 870. In an example using the Internet 890, a server 892 transmits program code for a particular application, requested by a message sent from computer 800, through Internet 890, ISP equipment 884, local network 880 and communications interface 870. The received code may be executed by processor 802 as it is received, or may be stored in storage device 808 or other non-volatile storage for later execution, or both. In this manner, computer system 800 may obtain application program code in the form of a signal on a carrier wave.

Various forms of computer readable media may be involved in carrying one or more sequence of instructions or data or both to processor 802 for execution. For example, instructions and data may initially be carried on a magnetic disk of a remote computer such as host 882. The remote computer loads the instructions and data into its dynamic memory and sends the instructions and data over a telephone line using a modem. A modem local to the computer system 800 receives the instructions and data on a telephone line and uses an infra-red transmitter to convert the instructions and data to a signal on an infra-red a carrier wave serving as the network link 878. An infrared detector serving as communications interface 870 receives the instructions and data carried in the infrared signal and places information representing the instructions and data onto bus 810. Bus 810 carries the information to memory 804 from which processor 802 retrieves and executes the instructions using some of the data sent with the instructions. The instructions and data received in memory 804 may optionally be stored on storage device 808, either before or after execution by the processor 802.

FIG. 9 illustrates a chip set 900 upon which an embodiment of the invention may be implemented. Chip set 900 is programmed to perform one or more steps of a method described herein and includes, for instance, the processor and memory components described with respect to FIG. 8 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 900, or a portion thereof, constitutes a means for performing one or more steps of a method described herein.

In one embodiment, the chip set 900 includes a communication mechanism such as a bus 901 for passing information among the components of the chip set 900. A processor 903 has connectivity to the bus 901 to execute instructions and process information stored in, for example, a memory 905. The processor 903 may include one or more processing cores with each core configured to perform independently. A multi-core processor enables multiprocessing within a single physical package. Examples of a multi-core processor include two, four, eight, or greater numbers of processing cores. Alternatively or in addition, the processor 903 may include one or more microprocessors configured in tandem via the bus 901 to enable independent execution of instructions, pipelining, and multithreading. The processor 903 may also be accompanied with one or more specialized components to perform certain processing functions and tasks such as one or more digital signal processors (DSP) 907, or one or more application-specific integrated circuits (ASIC) 909. A DSP 907 typically is configured to process real-world signals (e.g., sound) in real time independently of the processor 903. Similarly, an ASIC 909 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 903 and accompanying components have connectivity to the memory 905 via the bus 901. The memory 905 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 905 also stores the data associated with or generated by the execution of one or more steps of the methods described herein.

4. Alterations, Extensions, Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A method comprising:
a) receiving first data that indicates a perspective transform matrix corresponding to each of a plurality of different distances from a radiation source for particle therapy treatment based respectively on projected coordinates of a plurality of reference points from a digital image projector onto each of a plurality of different planes, wherein the digital image projector is mounted on a rotating gantry to which is rigidly fixed an output port from the radiation source and each of the plurality of different planes is perpendicular to an axis of a particle beam from the output port;
b) receiving second data that indicates a treatment plan for a subject, wherein the second data includes a body outline of the subject, a position of the subject on a couch, and, for each of a plurality of gantry orientations, a couch angle, an isocenter, and a plurality of target volumes inside the subject to which particle beam therapy is directed;
c) determining automatically on a processor a plurality of two-dimensional (2D) spot positions for a gantry orientation of the plurality of gantry orientations and a first couch angle based on the second data;
d) determining automatically on the processor for the gantry orientation a group of the plurality of 2D spot positions based on a common distance from the radiation source to the body outline;
e) determining automatically on the processor illuminated spots on a projection image based on the group of the plurality of 2D spot positions and the perspective transform matrix corresponding to a distance closest to the common distance; and
f) projecting the projection image from the image projector onto the subject on the couch when the gantry is at the gantry orientation and the couch is at the first couch angle.

2. A method as recited in claim 1, further comprising repeating steps d and e for a plurality of different groups based on a corresponding plurality of different common distances before projecting the projection image.

3. A method as recited in claim 1, further comprising repeating steps c and d and e and f for a plurality of different couch angles at the gantry orientation.

4. A method as recited in claim 1, further comprising repeating steps c and d and e and f and for a plurality of different gantry orientations.

5. A method as recited in claim 1, said determining spots on the projection image further comprising expanding sizes of spots to at least partially fill area between spots on the projection image.

6. A non-transitory computer-readable medium carrying one or more sequences of instructions, wherein execution of the one or more sequences of instructions by one or more processors causes the one or more processors to perform the steps of:
a) receiving first data that indicates a perspective transform matrix corresponding to each of a plurality of different distances from a radiation source output port based respectively on projected coordinates of a plurality of reference points from a digital image projector onto each of a plurality of different planes perpendicular to an axis of a particle beam from the radiation source output port at the plurality of different distances from the radiation source output port;
b) receiving second data that indicates a treatment plan for a subject, wherein the second data includes a body outline of the subject, a position of the subject on a couch, and, for each of a plurality of gantry orientations, a couch angle, an isocenter and one or more target volumes inside the subject to which particle beam therapy from a radiation source is directed;
c) determining a plurality of two dimensional (2D) spot positions for a gantry orientation of the plurality of gantry orientations and a first couch angle based on the second data;
d) determining for the gantry orientation a group of the plurality of 2D spot positions based on a common distance from the radiation source to the body outline;
e) determining illuminated spots on a projection image based on the group of the plurality of 2D spot positions and the perspective transform matrix corresponding to a distance closest to the common distance; and
f) projecting the projection image from the digital image projector onto the subject on the couch when the gantry is at the gantry orientation and the couch is at the first couch angle.

7. A computer-readable medium as recited in claim 6, said receiving first data further comprising determining the perspective transform matrix corresponding to each of the plurality of different distances from the radiation source output port.

8. A computer-readable medium as recited in claim 6, further comprising repeating steps d and e for a plurality of different groups based on a corresponding plurality of different common distances before projecting the projection image.

9. A computer-readable medium as recited in claim 6, further comprising repeating steps c and d and e and f for a plurality of different couch angles at the gantry orientation.

10. A computer-readable medium as recited in claim 6, further comprising repeating steps c and d and e and f for a plurality of different gantry orientations.

11. A computer-readable medium as recited in claim 6, said determining spots on the projection image further comprising expanding sizes of spots to at least partially fill area between spots on the projection image.

12. A system comprising:
a rotating gantry to which is rigidly fixed a radiation source output port for particle therapy treatment and a digital image projector;
a couch for supporting a subject in view of the radiation source output port;
at least one processor; and at least one memory including one or more sequences of instructions, the at least one memory and the one or more sequences of instructions configured to, with the at least one processor, cause the system to perform at least the following, a) receiving first data that indicates a perspective transform matrix corresponding to each of a plurality of different distances from the radiation source output port based respectively on projected coordinates of a plurality of reference points from the digital image projector onto each of a plurality of different planes perpendicular to an axis of a particle beam from the radiation source output port at the plurality of different distances from the radiation source output port;

b) receiving second data that indicates a treatment plan for a subject, wherein the second data includes a body outline of the subject, a position of the subject on a couch, and, for each of a plurality of gantry orientations, a couch angle, an isocenter and one or more target volumes inside the subject to which particle beam therapy from the radiation source output port is directed;

c) determining a plurality of two dimensional (2D) spot positions for a gantry orientation of the plurality of gantry orientations and a first couch angle based on the second data;

d) determining for the gantry orientation a group of the plurality of 2D spot positions based on a common distance from the radiation source output port to the body outline;

e) determining illuminated spots on a projection image based on the group of the plurality of 2D spot positions and the perspective transform matrix corresponding to a distance closest to the common distance; and f) projecting the projection image from the image projector onto the subject on the couch when the gantry is at the gantry orientation and the couch is at the first couch angle.

13. A system as recited in claim 12, said receiving first data further comprising determining the perspective transform matrix corresponding to each of the plurality of different distances from the radiation source output port.

14. A system as recited in claim 12, further comprising repeating steps d and e for a plurality of different groups based on a corresponding plurality of different common distances before projecting the projection image.

15. A system as recited in claim 12, further comprising repeating steps c and d and e and f for a plurality of different couch angles at the gantry orientation.

16. A system as recited in claim 12, further comprising repeating steps c and d and e and f for a plurality of different gantry orientations.

17. A system as recited in claim 12, said determining spots on the projection image further comprising expanding size of spots to at least partially fill area between spots on the projection image.

\* \* \* \* \*